(12) United States Patent
Khoury et al.

(10) Patent No.: US 11,698,582 B2
(45) Date of Patent: *Jul. 11, 2023

(54) METHOD FOR MODIFYING THE WETTABILITY AND/OR OTHER BIOCOMPATIBILITY CHARACTERISTICS OF A SURFACE OF A BIOLOGICAL MATERIAL BY THE APPLICATION OF GAS CLUSTER ION BEAM TECHNOLOGY AND BIOLOGICAL MATERIALS MADE THEREBY

(71) Applicant: Exogenesis Corporation, Billerica, MA (US)

(72) Inventors: Joseph B. Khoury, Dedham, MA (US); Laurence B. Tarrant, Beverly Farms, MA (US); Sean R. Kirkpatrick, Littleton, MA (US); Richard C. Svrluga, Billerica, MA (US)

(73) Assignee: Exogenesis Corporation, Billerica, MA (US)

( * ) Notice: Subject to any disclaimer, the term of this patent is extended or adjusted under 35 U.S.C. 154(b) by 263 days.

This patent is subject to a terminal disclaimer.

(21) Appl. No.: 16/239,272

(22) Filed: Jan. 3, 2019

(65) Prior Publication Data
US 2019/0137868 A1    May 9, 2019

Related U.S. Application Data

(60) Continuation-in-part of application No. 14/496,412, filed on Sep. 25, 2014, now Pat. No. 10,409,155, and (Continued)

(51) Int. Cl.
*H01J 37/05* (2006.01)
*H01J 37/317* (2006.01)
(Continued)

(52) U.S. Cl.
CPC .................. *G03F 1/80* (2013.01); *G03F 1/82* (2013.01); *H01J 37/05* (2013.01); *H01J 37/147* (2013.01); *H01J 37/317* (2013.01); *H01J 37/3171* (2013.01); *H01L 21/02115* (2013.01); *H01L 21/02274* (2013.01); *H01L 21/26506* (2013.01);
(Continued)

(58) Field of Classification Search
CPC .. A61F 2/08; A61F 2/28; A61F 2/0077; A61F 2250/0056; A61F 2002/0086; A61L 27/3604–3633; A61L 27/3683; A61L 27/3691–3695; A61L 2430/40; H05H 3/00–06; H01L 21/26566; H01J 37/317; H01J 2237/0812; H01J 2237/0041
See application file for complete search history.

(56) References Cited

U.S. PATENT DOCUMENTS

| 2004/0113093 A1* | 6/2004 | Mack ...................... H01J 37/08 |
| | | 250/396 R |
| 2006/0118731 A1* | 6/2006 | Saito ...................... H01J 37/08 |
| | | 250/427 |

(Continued)

*Primary Examiner* — Thaddeus B Cox
(74) *Attorney, Agent, or Firm* — Burns & Levinson, LLP; Jerry Cohen, Esq.

(57) ABSTRACT

A method for preparing a biological material for implanting provides irradiating at least a portion of the surface of the material with an accelerated Neutral Beam.

10 Claims, 14 Drawing Sheets

Related U.S. Application Data a continuation-in-part of application No. 14/238,752, filed as application No. PCT/US2012/051690 on Aug. 21, 2012, now abandoned, which is a division of application No. 13/215,514, filed on Aug. 23, 2011, now Pat. No. 8,847,148.

(60) Provisional application No. 61/526,179, filed on Aug. 22, 2011, provisional application No. 61/490,675, filed on May 27, 2011, provisional application No. 61/484,421, filed on May 10, 2011, provisional application No. 61/473,359, filed on Apr. 8, 2011, provisional application No. 61/376,225, filed on Aug. 23, 2010.

(51) Int. Cl.

| | | |
|---|---|---|
| *H01L 21/265* | (2006.01) | |
| *H01L 21/311* | (2006.01) | |
| *H01L 21/02* | (2006.01) | |
| *H05H 3/02* | (2006.01) | |
| *G03F 1/80* | (2012.01) | |
| *G03F 1/82* | (2012.01) | |
| *H01J 37/147* | (2006.01) | |
| *H01L 29/36* | (2006.01) | |
| *B24B 37/04* | (2012.01) | |

(52) U.S. Cl.
CPC .. *H01L 21/26513* (2013.01); *H01L 21/26566* (2013.01); *H01L 21/31105* (2013.01); *H01L 21/31111* (2013.01); *H05H 3/02* (2013.01); *B24B 37/04* (2013.01); *H01J 2237/0041* (2013.01); *H01J 2237/0812* (2013.01); *H01J 2237/15* (2013.01); *H01L 29/36* (2013.01); *Y10T 428/24355* (2015.01); *Y10T 428/24479* (2015.01); *Y10T 428/30* (2015.01)

(56) References Cited

U.S. PATENT DOCUMENTS

| | | | |
|---|---|---|---|
| 2008/0179537 A1* | 7/2008 | Saito | H01J 37/317 250/427 |
| 2010/0226958 A1* | 9/2010 | Khoury | A61L 27/3604 424/423 |
| 2012/0045615 A1* | 2/2012 | Kirkpatrick | H01J 37/05 428/141 |

* cited by examiner

METHOD FOR MODIFYING THE WETTABILITY AND/OR OTHER BIOCOMPATIBILITY CHARACTERISTICS OF A SURFACE OF A BIOLOGICAL MATERIAL BY THE APPLICATION OF GAS CLUSTER ION BEAM TECHNOLOGY AND BIOLOGICAL MATERIALS MADE THEREBY

FIELD OF THE INVENTION

This invention relates generally to biological materials intended for implant into a mammal and, more particularly to methods using beam technology for modifying the wettability and/or for improving the capability of the modified biological materials to 1) act as a host for cell attachment on a surface thereof; 2) to promote cell proliferation on a surface thereof or within the material; 3) to promote cell penetration through and beneath such surfaces, and/or; 4) to promote subsequent new tissue formation. Preferred beams are gas cluster ion beam and/or Neutral Beam derived from an accelerated gas cluster ion beam.

BACKGROUND OF THE INVENTION

Gas cluster ion beam (GCIB) irradiation has been used for nano-scale modification of surfaces. In the co-pending, commonly held U.S. patent application Ser. No. 12/210,018, "Method and System for Modifying the Wettability Characteristics of a Surface of a Medical Device by the Application of Gas Cluster Ion Beam Technology and Medical Devices Made Thereby", GCIB has been shown to modify the hydrophilic properties of non-biological material surfaces. GCIB processing has been well documented in the manufacturing of semiconductor devices and thin films. However, its potential uses for modifying surfaces of biological materials including tissues of the musculoskeletal system (e.g. bone, ligaments, tendons, rotator cuff, cartilage and such like), as well as for modification of other connective tissues such as epithelial tissue and endothelial tissue within major mammalian and avian organ systems are hitherto unknown. The physical modifications that GCIB processing produces on a ligament surface with respect to its capability to act as a host structure for cell attachment is hitherto unknown. It is generally known that anchorage dependent cells such as fibroblasts and osteoblasts benefit from hydrophilic surfaces to attach, grow, or differentiate well and they also prefer charged surfaces. With respect to hydrophilicity, droplet contact angle may be used as a measure of wettability, with decreasing contact angle measurements generally implying a more hydrophilic surface. Many methods have previously been employed to increase hydrophilicity or alter charge on non-biological surfaces, such as sandblasting, acid etching, plasma spraying of coatings, $CO_2$ laser smoothing and various forms of cleaning, including mechanical, ultrasonic, plasma, and chemical cleaning techniques. Other approaches have included the addition of surfactants or the application of films or coatings having different wettability characteristics. The preparation of surfaces of biological materials by GCIB or Neutral Beam irradiation for enhanced cellular attachment either through increasing the hydrophilicity of a surface or by modifying the surface charge state or surface chemistry, or by other mechanisms has not been previously demonstrated.

Beams of energetic conventional ions, accelerated electrically charged atoms or molecules, are widely utilized to form semiconductor device junctions, to modify surfaces by sputtering, and to modify the properties of thin films. Unlike conventional ions, gas cluster ions are formed from clusters of large numbers (having a typical distribution of several hundreds to several thousands with a mean value of a few thousand) of weakly bound atoms or molecules of materials that are gaseous under conditions of standard temperature and pressure (commonly oxygen, nitrogen, or an inert gas such as argon, for example, but any condensable gas can be used to generate gas cluster ions) with each cluster ion sharing one or more electrical charges, and which are accelerated together through high voltages (on the order of from about 3 kV to about 70 kV or more) to have high total energies. After gas cluster ions have been formed and accelerated, their charge states may be altered or become altered (even neutralized), and they may fragment into smaller cluster ions and/or neutralized smaller clusters, but they tend to retain the relatively high total energies that result from having previously been accelerated through high voltages. Gas cluster ion beams have been used to process surfaces of non-biological materials for purposes of cleaning, etching, smoothing, film growth, and the like. They are well known for their smoothing effects on most solid material surfaces and have been employed for smoothing materials such as diamond, silicon, and metals. Because of the large number of atoms or molecules in each gas cluster ion, and because they are weakly bound, their effect upon striking a surface is very shallow, unlike the effect of conventional (monomer or molecular) ions. The cluster is disrupted at impact and each atom or molecule then carries only a relatively few eV of energy compared to the total energy of the accelerated cluster. Instantaneous temperatures and pressures can be very high at gas cluster ion impact sites, and a variety of surface chemistry, etching, and other effects can occur. Surface chemistry may be modified by GCIB or Neutral Beam irradiation (for example) by exposing surface bonds (thus modifying surface charge states) and/or by incorporation of reactive atoms or molecules from the gas cluster ions into the surface (by using gas cluster ions comprising reactive atoms or molecules such as oxygen, nitrogen, carbon, etc.) However, these effects are very superficial, extending, at most, some tens of Angstroms beneath the impact site and accordingly there is no significant damage to any material located deeper below the superficial surface impact site.

It is therefore an object of this invention to provide methods for increasing the wettability and/or altering the chemistry or charge state and/or modifying other physical characteristics of a surface of a biological material by the application of gas cluster ion beam technology in the form of a gas cluster ion beam irradiation or accelerated Neutral Beam irradiation.

It is a further object of this invention to provide methods for preparing a surface of a biological material for attachment, proliferation, migration, etc. of new cellular growth, by the application of gas cluster ion beam technology in the form of a gas cluster ion beam irradiation and/or accelerated Neutral Beam irradiation, and optionally, for the stimulation of the new cells to differentiate into tissue such as bone, fibrous connective tissue, epithelium, endothelium or the like.

Another object of this invention to provide methods for increasing the wettability of a portion of a surface of a biological material and/or for preparing a surface of the biological material for attachment, proliferation, migration, etc. of new cellular growth, in a controlled pattern, by the application of gas cluster ion beam technology in the form of a gas cluster ion beam irradiation and/or accelerated Neutral Beam irradiation.

A still further object of this invention to provide a surgically implantable biological material that has a surface or surface portion with increased hydrophilicity and/or that has a surface with an enhanced capability for cell penetration and/or to act as a host for new cellular attachment, growth, and differentiation, by the application of gas cluster ion beam technology in the form of a gas cluster ion beam irradiation and/or accelerated Neutral Beam irradiation, and optionally, for the stimulation of the new cells to differentiate into tissue such as bone, fibrous connective tissue, epithelium, endothelium or the like.

Another object of this invention is to provide a biological material for surgical implantation and/or graft as well as a method for preparation and surgical implantation of a biological material graft incorporating a specific cellular material in the graft, and optionally for stimulating the specific cellular material to differentiate into tissue such as bone, fibrous connective tissue, epithelium, endothelium, or the like.

SUMMARY OF THE INVENTION

The objects set forth above as well as further and other objects and advantages of the present invention are achieved by the invention described hereinbelow.

As used herein, the terms "GCIB", "gas cluster ion beam" and "gas cluster ion" are intended to encompass not only ionized beams and ions, but also accelerated beams and ions that have had all or a portion of their charge states modified (including neutralized) following their acceleration. The terms "GCIB" and "gas cluster ion beam" are intended to encompass all beams that comprise accelerated gas cluster ions even though they may also comprise non-clustered particles. As used herein, the term "Neutral Beam" is intended to mean a beam of neutral gas clusters and/or neutral monomers derived from an accelerated gas cluster ion beam and wherein the acceleration results from acceleration of a gas cluster ion beam. As used herein, the term "monomer" refers equally to either a single atom or a single molecule. The terms "atom," "molecule," and "monomer" may be used interchangeably and all refer to the appropriate monomer that is characteristic of the gas under discussion (either a component of a cluster, a component of a cluster ion, or an atom or molecule). For example, a monatomic gas like argon may be referred to in terms of atoms, molecules, or monomers and each of those terms means a single atom. Likewise, in the case of a diatomic gas like nitrogen, it may be referred to in terms of atoms, molecules, or monomers, each term meaning a diatomic molecule. Furthermore a molecular gas like $CO_2$, may be referred to in terms of atoms, molecules, or monomers, each term meaning a three atom molecule, and so forth. These conventions are used to simplify generic discussions of gases and gas clusters or gas cluster ions independent of whether they are monatomic, diatomic, or molecular in their gaseous form.

Ions have long been favored for many processes because their electric charge facilitates their manipulation by electrostatic and magnetic fields. This introduces great flexibility in processing. However, in some applications, the charge that is inherent to any ion (including gas cluster ions in a GCIB) may produce undesirable effects in the processed surfaces. GCIB has a distinct advantage over conventional ion beams in that a gas cluster ion with a single or small multiple charge enables the transport and control of a much larger mass-flow (a cluster may consist of hundreds or thousands of molecules) compared to a conventional ion (a single atom, molecule, or molecular fragment.) Particularly in the case of insulating materials, surfaces processed using ions often suffer from charge-induced damage resulting from abrupt discharge of accumulated charges, or production of damaging electrical field-induced stress in the material (again resulting from accumulated charges.) In many such cases, GCIBs have an advantage due to their relatively low charge per mass, but in some instances may not eliminate the target-charging problem. Furthermore, moderate to high current intensity ion beams may suffer from a significant space charge-induced defocusing of the beam that tends to inhibit transporting a well-focused beam over long distances. Again, due to their lower charge per mass relative to conventional ion beams, GCIBs have an advantage, but they do not fully eliminate the space charge transport problem.

A further instance of need or opportunity arises from the fact that although the use of beams of neutral molecules or atoms provides benefit in some surface processing applications and in space charge-free beam transport, it has not generally been easy and economical to produce intense beams of neutral molecules or atoms except for the case of nozzle jets, where the energies are generally on the order of a few milli-electron-volts per atom or molecule, and thus have limited processing capabilities. More energetic neutral particles can be beneficial or necessary in many applications, for example when it is desirable to break surface or shallow subsurface bonds to facilitate cleaning, etching, smoothing, deposition, amorphization, or to produce surface chemistry effects. In such cases, energies of from about an eV up to a few thousands of eV per particle can often be useful. Methods and apparatus for forming such Neutral Beams by first forming an accelerated charged GCIB and then neutralizing or arranging for neutralization of at least a fraction of the beam and separating the charged and uncharged fractions are disclosed herein. The Neutral Beams may consist of neutral gas clusters, neutral monomers, or a combination of both. Although GCIB processing has been employed successfully for many applications, there are new and existing application needs not fully met by GCIB or other state of the art methods and apparatus, and wherein accelerated neutral beams may provide superior results. For example, in many situations, while a GCIB can produce dramatic atomic-scale smoothing of an initially somewhat rough surface, the ultimate smoothing that can be achieved is often less than the required smoothness, and in other situations GCIB processing can result in roughening moderately smooth surfaces rather than smoothing them further.

When accelerated gas cluster ions are fully dissociated and neutralized, the resulting neutral monomers will have energies approximately equal to the total energy of the original accelerated gas cluster ion, divided by the number, $N_1$, of monomers that comprised the original gas cluster ion at the time it was accelerated. Such dissociated neutral monomers will have energies on the order of from about 1 eV to tens or even a as much as a few thousands of eV, depending on the original accelerated energy of the gas cluster ion and the size of the gas cluster at the time of acceleration.

Gas cluster ion beams are generated and transported for purposes of irradiating a workpiece according to known techniques. Various types of holders are known in the art for holding the object in the path of the GCIB for irradiation and for manipulating the object to permit irradiation of a multiplicity of portions of the object. Neutral Beams may be generated and transported for purposes of irradiating a workpiece according to techniques taught herein.

The present invention may employ a high beam purity method and system for deriving from an accelerated gas cluster ion beam an accelerated neutral gas cluster and/or preferably monomer beam that can be employed for a variety of types of surface and shallow subsurface materials processing and which is capable, for many applications, of superior performance compared to conventional GCIB processing. It can provide well-focused, accelerated, intense neutral monomer beams with particles having energies in the range of from about 1 eV to as much as a few thousand eV. This is an energy range in which it has heretofore been impractical with simple, relatively inexpensive apparatus to form intense neutral beams.

These accelerated Neutral Beams are generated by first forming a conventional accelerated GCIB, then partly or essentially fully dissociating it by methods and operating conditions that do not introduce impurities into the beam, then separating the remaining charged portions of the beam from the neutral portion, and subsequently using the resulting accelerated Neutral Beam for workpiece processing. Depending on the degree of dissociation of the gas cluster ions, the Neutral Beam produced may be a mixture of neutral gas monomers and gas clusters or may essentially consist entirely or almost entirely of neutral gas monomers. It is preferred that the accelerated Neutral Beam is a fully dissociated neutral monomer beam.

An advantage of the Neutral Beams that may be produced by the methods and apparatus of this invention, is that they may be used to process electrically insulating materials without producing damage to the material due to charging of the surfaces of such materials by beam transported charges as commonly occurs for all ionized beams including GCIB. For example, in semiconductor and other electronic applications, ions often contribute to damaging or destructive charging of thin dielectric films such as oxides, nitrides, etc. The use of Neutral Beams can enable successful beam processing of polymer, dielectric, and/or other electrically insulating or high electrical resistivity materials, coatings, and films in applications where ion beams produce undesired side effects due to surface or other charging effects. Examples include (without limitation) processing of corrosion inhibiting coatings, and irradiation cross-linking and/or polymerization of organic films. In other examples, Neutral Beam induced modifications of polymer or other dielectric materials (e.g. sterilization, smoothing, improving surface biocompatibility, and improving attachment of and/or control of elution rates of drugs) may enable the use of such materials in medical devices for implant and/or other medical/surgical applications. Further examples include Neutral Beam processing of glass, polymer, and ceramic bio-culture labware and/or environmental sampling surfaces where such beams may be used to improve surface characteristics like, for example, roughness, smoothness, hydrophilicity, and biocompatibility.

Since the parent GCIB, from which accelerated Neutral Beams may be formed by the methods and apparatus of the invention, comprises ions it is readily accelerated to desired energy and is readily focused using conventional ion beam techniques. Upon subsequent dissociation and separation of the charged ions from the neutral particles, the Neutral Beam particles tend to retain their focused trajectories and may be transported for extensive distances with good effect.

When neutral gas clusters in a jet are ionized by electron bombardment, they become heated and/or excited. This may result in subsequent evaporation of monomers from the ionized gas cluster, after acceleration, as it travels down the beamline. Additionally, collisions of gas cluster ions with background gas molecules in the ionizer, accelerator and beamline regions, also heat and excite the gas cluster ions and may result in additional subsequent evolution of monomers from the gas cluster ions following acceleration. When these mechanisms for evolution of monomers are induced by electron bombardment and/or collision with background gas molecules (and/or other gas clusters) of the same gas from which the GCIB was formed, no contamination is contributed to the beam by the dissociation processes that results in evolving the monomers.

There are other mechanisms that can be employed for dissociating (or inducing evolution of monomers from) gas cluster ions in a GCIB without introducing contamination into the beam. Some of these mechanisms may also be employed to dissociate neutral gas clusters in a neutral gas cluster beam. One mechanism is laser irradiation of the cluster-ion beam using infra-red or other laser energy. Laser-induced heating of the gas cluster ions in the laser irradiated GCIB results in excitement and/or heating of the gas cluster ions and causes subsequent evolution of monomers from the beam. Another mechanism is passing the beam through a thermally heated tube so that radiant thermal energy photons impact the gas cluster ions in beam. The induced heating of the gas cluster ions in by the radiant thermal energy in the tube results in excitement and/or heating of the gas cluster ions and causes subsequent evolution of monomers from the beam. In another mechanism, crossing the gas cluster ion beam by a gas jet of the same gas or mixture as the source gas used in formation of the GCIB (or other non-contaminating gas) results in collisions of monomers of the gas in the gas jet with the gas clusters in the ion beam producing excitement and/or heating of the gas cluster ions in the beam and subsequent evolution of monomers from the excited gas cluster ions. By depending entirely on electron bombardment during initial ionization and/or collisions (with other cluster ions, or with background gas molecules of the same gas(es) as those used to form the GCIB) within the beam and/or laser or thermal radiation and/or crossed jet collisions of non-contaminating gas to produce the GCIB dissociation and/or fragmentation, contamination of the beam by collision with other materials is avoided.

As a neutral gas cluster jet from a nozzle travels through an ionizing region where electrons are directed to ionize the clusters, a cluster may remain un-ionized or may acquire a charge state, q, of one or more charges (by ejection of electrons from the cluster by an incident electron). The ionizer operating conditions influence the likelihood that a gas cluster will take on a particular charge state, with more intense ionizer conditions resulting in greater probability that a higher charge state will be achieved. More intense ionizer conditions resulting in higher ionization efficiency may result from higher electron flux and/or higher (within limits) electron energy. Once the gas cluster has been ionized, it is typically extracted from the ionizer, focused into a beam, and accelerated by falling through an electric field. The amount of acceleration of the gas cluster ion is readily controlled by controlling the magnitude of the accelerating electric field. Typical commercial GCIB processing tools generally provide for the gas cluster ions to be accelerated by an electric field having an adjustable accelerating potential, $V_{Acc}$, typically of, for example, from about 1 kV to 70 kV (but not limited to that range—$V_{Acc}$ up to 200 kV or even more may be feasible). Thus a singly charged gas cluster ion achieves an energy in the range of from 1 to 70 keV (or more if larger $V_{Acc}$ is used) and a multiply charged (for example, without limitation, charge state, q=3 electronic charges) gas cluster ion achieves an energy in the range of from 3 to 210 keV (or more for higher $V_{Acc}$). For other gas cluster ion charge states and acceleration potentials, the accelerated energy per cluster is $qV_{Acc}$ eV. From a given ionizer with a given ionization efficiency, gas cluster ions will have a distribution of charge states from zero (not ionized) to a higher number such as for example 6 (or with high ionizer efficiency, even more), and the most probable and mean values of the charge state distribution also increase with increased ionizer efficiency (higher electron flux and/or energy). Higher ionizer efficiency also results in increased numbers of gas cluster ions being formed in the ionizer. In many cases, GCIB processing throughput increases when operating the ionizer at high efficiency results in increased GCIB current. A downside of such operation is that multiple charge states that may occur on intermediate size gas cluster ions can increase crater and/or rough interface formation by those ions, and often such effects may operate counterproductively to the intent of the processing. Thus for many GCIB surface processing recipes, selection of the ionizer operating parameters tends to involve more considerations than just maximizing beam current. In some processes, use of a "pressure cell" (see U.S. Pat. No. 7,060,989, to Swenson et al.) may be employed to permit operating an ionizer at high ionization efficiency while still obtaining acceptable beam processing performance by moderating the beam energy by gas collisions in an elevated pressure "pressure cell." Techniques of the present invention avoid the use of an elevated pressure "pressure cell."

With the present invention there is no downside to operating the ionizer at high efficiency—in fact such operation is sometimes preferred. When the ionizer is operated at high efficiency, there may be a wide range of charge states in the gas cluster ions produced by the ionizer. This results in a wide range of velocities in the gas cluster ions in the extraction region between the ionizer and the accelerating electrode, and also in the downstream beam. This may result in an enhanced frequency of collisions between and among gas cluster ions in the beam that generally results in a higher degree of fragmentation of the largest gas cluster ions. Such fragmentation may result in a redistribution of the cluster sizes in the beam, skewing it toward the smaller cluster sizes. These cluster fragments retain energy in proportion to their new size (N) and so become less energetic while essentially retaining the accelerated velocity of the initial unfragmented gas cluster ion. The change of energy with retention of velocity following collisions has been experimentally verified (as for example reported in Toyoda, N. et al., "Cluster size dependence on energy and velocity distributions of gas cluster ions after collisions with residual gas," Nucl. Instr. & Meth. in Phys. Research B 257 (2007), pp 662-665). Fragmentation may also result in redistribution of charges in the cluster fragments. Some uncharged fragments likely result and multi-charged gas cluster ions may fragment into several charged gas cluster ions and perhaps some uncharged fragments. It is understood by the inventors that design of the focusing fields in the ionizer and the extraction region may enhance the focusing of the smaller gas cluster ions and monomer ions to increase the likelihood of collision with larger gas cluster ions in the beam extraction region and in the downstream beam, thus contributing to the dissociation and/or fragmenting of the gas cluster ions.

In an embodiment of the present invention, background gas pressure in the ionizer, acceleration region, and beamline may optionally be arranged to have a higher pressure than is normally utilized for good GCIB transmission. This can result in additional evolution of monomers from gas cluster ions (beyond that resulting from the heating and/or excitement resulting from the initial gas cluster ionization event). Pressure may be arranged so that gas cluster ions have a short enough mean-free-path and a long enough flight path between ionizer and workpiece that they must undergo multiple collisions with background gas molecules.

For a homogeneous gas cluster ion containing N monomers and having a charge state of q and which has been accelerated through an electric field potential drop of $V_{Acc}$ volts, the cluster will have an energy of approximately $qV_{Acc}/N_1$ eV per monomer, where $N_1$ is the number of monomers in the cluster ion at the time of acceleration. Except for the smallest gas cluster ions, a collision of such an ion with a background gas monomer of the same gas as the cluster source gas will result in additional deposition of approximately $qV_{Acc}/N_1$ eV into the gas cluster ion. This energy is relatively small compared to the overall gas cluster ion energy ($qV_{Acc}$) and generally results in excitation or heating of the cluster and in subsequent evolution of monomers from the cluster. It is believed that such collisions of larger clusters with background gas seldom fragment the cluster but rather heats and/or excites it to result in evolution of monomers by evaporation or similar mechanisms. Regardless of the source of the excitation that results in the evolution of a monomer or monomers from a gas cluster ion, the evolved monomer(s) have approximately the same energy per particle, $qV_{Acc}/N_1$ eV, and retain approximately the same velocity and trajectory as the gas cluster ion from which they have evolved. When such monomer evolutions occur from a gas cluster ion, whether they result from excitation or heating due to the original ionization event, a collision, or radiant heating, the charge has a high probability of remaining with the larger residual gas cluster ion. Thus after a sequence of monomer evolutions, a large gas cluster ion may be reduced to a cloud of co-traveling monomers with perhaps a smaller residual gas cluster ion (or possibly several if fragmentation has also occurred). The co-traveling monomers following the original beam trajectory all have approximately the same velocity as that of the original gas cluster ion and each has energy of approximately $qV_{Acc}/N_1$ eV. For small gas cluster ions, the energy of collision with a background gas monomer is likely to completely and violently dissociate the small gas cluster and it is uncertain whether in such cases the resulting monomers continue to travel with the beam or are ejected from the beam.

Prior to the GCIB reaching the workpiece, the remaining charged particles (gas cluster ions, particularly small and intermediate size gas cluster ions and some charged monomers, but also including any remaining large gas cluster ions) in the beam are separated from the neutral portion of the beam, leaving only a Neutral Beam for processing the workpiece.

In typical operation, a ratio of energy in the Neutral Beam to energy in the full (charged plus neutral) beam delivered at the processing target is in the range of from about 50% to 95%, so by the methods and apparatus of the present invention it is possible to convert the majority of the kinetic energy of the full accelerated charged beam to that of a Neutral Beam.

The dissociation of the gas cluster ions and thus the production of high neutral monomer beam energy is facilitated by 1) Operating at higher acceleration voltages. This increases $qV_{Acc}/N$ for any given cluster size. 2) Operating at high ionizer efficiency. This increases $qV_{Acc}/N$ for any given cluster size by increasing q and increases cluster-ion on cluster-ion collisions in the extraction region due to the differences in charge states between clusters; 3) Operating at a high ionizer, acceleration region, or beamline pressure or operating with a gas jet crossing the beam, or with a longer beam path, all of which increase the probability of background gas collisions for a gas cluster ion of any given size; 4) Operating with laser irradiation or thermal radiant heating of the beam, which directly promote evolution of monomers from the gas cluster ions; and 5) Operating at higher nozzle gas flow, which increases transport of gas, clustered and perhaps unclustered into the GCIB trajectory, which increases collisions resulting in greater evolution of monomers.

Measurement of the Neutral Beam cannot be made by current measurement as is convenient for gas cluster ion beams. A Neutral Beam power sensor is used to facilitate dosimetry when irradiating a workpiece with a Neutral Beam. The Neutral Beam sensor is a thermal sensor that intercepts the beam (or optionally a known sample of the beam). The rate of rise of temperature of the sensor is related to the energy flux resulting from energetic beam irradiation of the sensor. The thermal measurements must be made over a limited range of temperatures of the sensor to avoid errors due to thermal re-radiation of the energy incident on the sensor. For a GCIB process, the beam power (watts) is equal to the beam current (amps) times $V_{Acc}$, the beam acceleration voltage. When a GCIB irradiates a workpiece for a period of time (seconds), the energy (joules) received by the workpiece is the product of the beam power and the irradiation time. The processing effect of such a beam when it processes an extended area is distributed over the area (for example, $cm^2$). For ion beams, it has been conveniently conventional to specify a processing dose in terms of irradiated ions/$cm^2$, where the ions are either known or assumed to have at the time of acceleration an average charge state, q, and to have been accelerated with through a potential difference of, $V_{Acc}$ volts, so that each ion carries an energy of q $V_{Acc}$ eV (an eV is approximately $1.6 \times 10^{-19}$ joule). Thus an ion beam dose for an average charge state, q, accelerated by $V_{Acc}$ and specified in ions/$cm^2$ corresponds to a readily calculated energy dose expressible in joules/$cm^2$. For an accelerated neutral beam derived from an accelerated GCIB as utilized in the present invention, the value of q at the time of acceleration and the value of $V_{Acc}$ is the same for both of the (later-formed and separated) charged and uncharged fractions of the beam. The power in the two (neutral and charged) fractions of the GCIB divides proportional to the mass in each beam fraction. Thus for the accelerated Neutral Beam as employed in the invention, when equal areas are irradiated for equal times, the energy dose (joules/$cm^2$) deposited by the Neutral Beam is necessarily less than the energy dose deposited by the full GCIB. By using a thermal sensor to measure the power in the full GCIB $P_G$ and that in the Neutral Beam $P_N$ (which is commonly found to be about 50% to 95% that of the full GCIB) it is possible to calculate a compensation for use in the Neutral Beam processing dosimetry. When $P_N$ is $aP_G$, then the compensation factor is, k=1/a. Thus if a workpiece is processed using a Neutral Beam derived from a GCIB, for a time duration is made to be k times greater than the processing duration for the full GCIB (including charged and neutral beam portions) required to achieve a dose of D ions/$cm^2$, then the energy doses deposited in the workpiece by both the Neutral Beam and the full GCIB are the same (though the results may be different due to qualitative differences in the processing effects due to differences of particle sizes in the two beams.) As used herein, a Neutral Beam process dose compensated in this way is sometimes described as having an energy/$cm^2$ equivalence of a dose of D ions/$cm^2$.

Use of a Neutral Beam derived from a gas cluster ion beam in combination with a thermal power sensor for dosimetry in many cases has advantages compared with the use of the full gas cluster ion beam or an intercepted or diverted portion, which inevitably comprises a mixture of gas cluster ions and neutral gas clusters and/or neutral monomers, and which is conventionally measured for dosimetry purposes by using a beam current measurement. Some advantages are as follows:

1) The dosimetry can be more precise with the Neutral Beam using a thermal sensor for dosimetry because the total power of the beam is measured. With a GCIB employing the traditional beam current measurement for dosimetry, only the contribution of the ionized portion of the beam is measured and employed for dosimetry. Minute-to-minute and setup-to-setup changes to operating conditions of the GCIB apparatus may result in variations in the fraction of neutral monomers and neutral clusters in the GCIB. These variations can result in process variations that may be less controlled when the dosimetry is done by beam current measurement.

2) With a Neutral Beam, any material may be processed, including highly insulating materials and other materials that may be damaged by electrical charging effects, without the necessity of providing a source of target neutralizing electrons to prevent workpiece charging due to charge transported to the workpiece by an ionized beam. When employed with conventional GCIB, target neutralization to reduce charging is seldom perfect, and the neutralizing electron source itself often introduces problems such as workpiece heating, contamination from evaporation or sputtering in the electron source, etc. Since a Neutral Beam does not transport charge to the workpiece, such problems are reduced.

3) There is no necessity for an additional device such as a large aperture high strength magnet to separate energetic monomer ions from the Neutral Beam. In the case of conventional GCIB the risk of energetic monomer ions (and other small cluster ions) being transported to the workpiece, where they penetrate producing deep damage, is significant and an expensive magnetic filter is routinely required to separate such particles from the beam. In the case of the Neutral Beam apparatus of the invention, the separation of all ions from the beam to produce the Neutral Beam inherently removes all monomer ions.

The present invention applies gas cluster ion beam (GCIB) technology to the processing of a surface or a portion of a surface of a biological material to modify its surface properties such as the hydrophilicity or the degree of wettability of the surface and/or to improve the suitability of the surface or a portion of the surface to act as a host for new cellular growth and/or attachment to biological materials including tissues of the musculoskeletal system, e.g. bone, ligaments, tendons, rotator cuff, cartilage and the like. Either a GCIB or an accelerated neutral beam derived from an accelerated GCIB may be employed for processing the surface. Through the use of masking techniques or by controlling the incidence of the GCIB or Neutral Beam onto the surface or by other means of controlling the spatial extent of the GCIB or Neutral Beam processing, the surface characteristics may be modified in a controlled pattern with desired regions modified and other regions unmodified. Thus, cellular attachment to the biological material (when surgically implanted) may be facilitated at the desired regions, without encouraging cellular attachment at regions where it is not appropriate to a successful surgical outcome.

The inventors have processed surfaces of tissues of the musculoskeletal system e.g. bone and ligament (in both natural and decellularized states) with GCIB and Neutral Beam techniques and have found that certain types of GCIB or Neutral Beam processing result in increasing the hydrophilicity of the surfaces of the biological materials and in improving the suitability of the surfaces for new cellular growth and attachment. The examples given herein are structural tissues but the invention is not limited to structural tissue.

For producing patterned surface variations, the GCIB or Neutral Beam processing may be controlled using masks or beam writing techniques, or various other means for controlling the exposure of the workpiece surfaces to GCIB or Neutral Beam processing in such a way as to restrict processing to certain regions of the surface or to produce differing types of GCIB or Neutral Beam processing in differing regions of the workpiece. Masks employed may be mechanical masks that shadow portions of the workpiece from GCIB or Neutral Beam processing. The achievement of patterned surface variations is not limited to the use of mechanical masks.

One embodiment of the present invention provides a method for preparing a biological material for implanting, said method comprising providing a reduced pressure chamber, forming a first accelerated Neutral Beam within said reduced pressure chamber, providing a holder within said reduced pressure chamber for holding a biological material, positioning said biological material in said holder in said reduced pressure chamber, and irradiating at least a first portion of a surface of said biological material with said first accelerated Neutral Beam, wherein said biological material undergoes a change in properties.

The change in properties may comprise a change selected from the group consisting of increased wettability of said at least a first portion of said surface, increased hydrophilicity of said at least a first portion of said surface, modified chemistry of said at least a first portion of said surface, and modified charge state of said at least a first portion of the surface. The method may further comprise exposing said biological material to living cells, wherein said living cells exhibit a behavior selected from the group consisting of increased attachment to said at least a first portion of said surface, increased proliferation on said at least a first portion of said surface, increased penetration through or beneath said at least a first portion of said surface, and increased formation on or beneath said at least a first portion of said surface. The biological tissue may comprise a tissue selected from the group consisting of a musculoskeletal system tissue, a connective tissue, a bone tissue, a tendon tissue, a ligament tissue, a cartilage tissue, an epithelial tissue, and an endothelial tissue. The biological material may comprise a cellular tissue or a decellularized tissue. The biological material may comprise a mammalian tissue or an avian tissue. The first accelerated Neutral Beam may be derived from a first accelerated gas cluster ion beam. The first gas cluster ion beam may comprise gas cluster ions comprising atoms selected from the group consisting of argon, neon, xenon, nitrogen, carbon, and oxygen.

The method may further comprise forming a second accelerated cluster ion beam within the reduced pressure chamber, and irradiating at least a second portion of said surface or said biological material with said second accelerated Neutral Beam.

The first gas accelerated Neutral Beam may be derived from an accelerated gas cluster ion beam having a first gas cluster ion composition and a first gas cluster ion beam acceleration potential, and the second accelerated Neutral Beam may be derived from a gas cluster ion beam having a second gas cluster ion composition and a second gas cluster ion beam acceleration potential, and irradiating said at least a first portion of said surface comprises irradiating with a first accelerated Neutral Beam dose, and irradiating said at least a second portion of said surface comprises irradiating with a second accelerated Neutral Beam dose.

The method may further comprise exposing said biological tissue to living cells, wherein at least a third portion of said surface is not irradiated, and wherein said living cells exposed to said at least a first portion, when compared to said living cells exposed to said at least a third portion, exhibit different behavior, said behavior comprising properties selected from the group consisting of surface attachment, cell proliferation, cell surface penetration, and tissue formation.

Another embodiment of the present invention provides a method for surgical grafting of a tissue, the method comprising explanting a graft tissue from a donor, irradiating at least a first portion of said graft tissue with an accelerated Neutral Beam, and surgically grafting said graft tissue into a recipient. The recipient may be a mammal and said graft tissue may be an allograft, an autograft or a xenograft. The graft tissue may be a ligament tissue or a tendon tissue or a bone tissue.

The method may further comprise lyophilizing said graft tissue prior to said irradiating.

The method may further comprise reconstituting said graft tissue after said lyophilizing and said irradiating, and prior to said surgical grafting. The step of surgical grafting may include bringing said at least a second portion into contact with a fluid or cells from said recipient for in situ reconstitution or seeding. The method may further comprise at least partially decellularizing at least a second portion of said graft tissue prior to said irradiating, wherein said first portion comprises at least a part of said second portion. The method may further comprise harvesting cells for seeding and seeding at least a third portion of said at least a first portion with the harvested cells, prior to said surgical grafting. The harvested cells may be harvested from said recipient. The method may further comprise exposing, prior to surgical grafting, the graft tissue to a composition comprising a component selected from the group consisting of a growth factor, a cytokine, a differentiation factor, a demineralized bone powder, and stem cells.

For a better understanding of the present invention, together with other and further objects thereof, reference is made to the accompanying drawings and detailed description and its scope will be pointed out in the appended claims.

DETAILED DESCRIPTION OF INVENTION

In the following description, for simplification, item numbers from earlier-described figures may appear in subsequently-described figures without discussion. Likewise, items discussed in relation to earlier figures may appear in subsequent figures without item numbers or additional description. In such cases items with like numbers are like items and have the previously-described features and functions, and illustration of items without item numbers shown in the present figure refer to like items having the same functions as the like items illustrated in earlier-discussed numbered figures.

Figure 1:
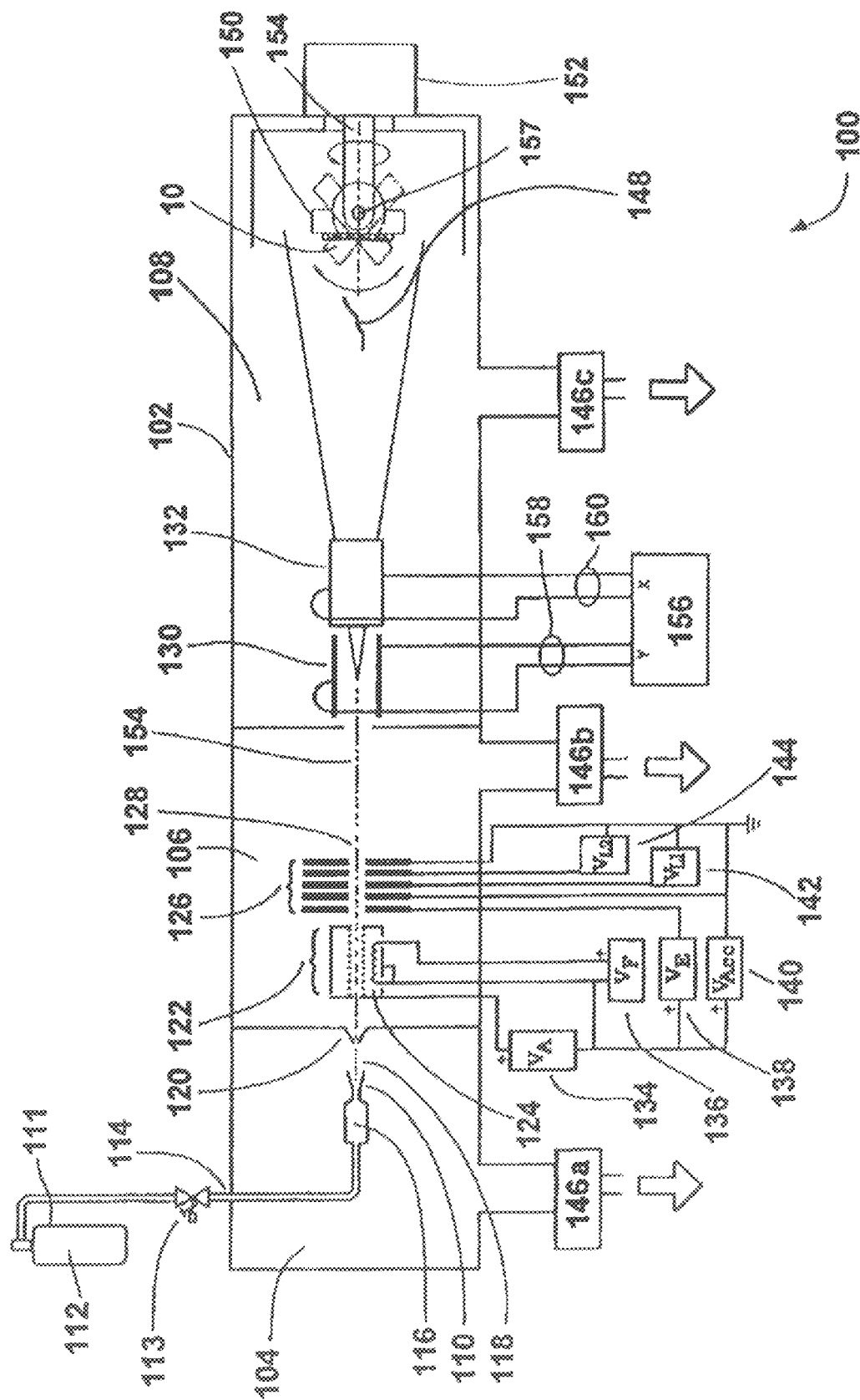
FIG. 1 is a schematic view of a gas cluster ion beam processing system 100 of a type known in the GCIB art and suitable for practicing the invention.

Reference is made to FIG. 1 of the drawings, which shows a typical gas cluster ion beam (GCIB) processor 100 of a type known in prior art for surface processing. Although not limited to the specific components described herein, the processor 100 is made up of a vacuum vessel 102 which is divided into three communicating chambers, a source chamber 104, an ionization/acceleration chamber 106, and a processing chamber 108 which includes therein a workpiece holder 150 capable of positioning a workpiece 10 for processing by a gas cluster ion beam.

During use, the three chambers are evacuated to suitable operating pressures by vacuum pumping systems 146a, 146b, and 146c, respectively. A condensable source gas 112 (for example argon or $N_2$) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion in the jet, causes a portion of the gas jet 118 to condense into clusters, most consisting of from a few hundred to several thousand (or even tens of thousands) weakly bound atoms or molecules. A gas skimmer aperture 120 partially separates the gas molecules that have not condensed into a cluster jet from the cluster jet so as to minimize pressure in the downstream regions where such higher pressures would be detrimental (e.g., ionizer 122, high voltage electrodes 126, and process chamber 108). Suitable condensable source gases 112 include, but are not necessarily limited to inert gases (such as argon), nitrogen, carbon dioxide, and oxygen.

After the supersonic gas jet 118 containing gas clusters has been formed, the clusters are ionized in an ionizer 122. The ionizer 122 may be an electron impact ionizer that produces thermoelectrons from one or more incandescent filaments 124 and accelerates and directs the electrons causing them to collide with the gas clusters in the gas jet 118, where the jet passes through the ionizer 122. The electron impact ejects electrons from the clusters, causing a portion the clusters to become positively ionized. A set of suitably biased high voltage electrodes 126 extracts the cluster ions from the ionizer 122, forming a beam, then accelerates the cluster ions with an acceleration potential (typically from 1 kV to as much as several tens of kV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCIB 128. Accelerator power supply 140 provides voltage $V_{Acc}$ to bias a high voltage electrode with respect to the ionizer 122 so as to result in a total GCIB acceleration potential equal to $V_{Acc}$ volts (V). One or more lens power supplies (142 and 144, for example) may be provided to bias high voltage electrodes with potentials ($V_{L1}$ and $V_{L2}$ for example) to focus the GCIB 128.

A workpiece 10 to be processed by the GCIB processor 100 is held on a workpiece holder 150, disposed in the path of the GCIB 128. An optional retainer 12 that may be a clip or clamp or other retaining item may be employed to retain the workpiece 10 in an attached position on the workpiece holder 150. In order for uniform processing of the workpiece 10 to take place, the workpiece holder 150 is designed in a manner set forth below to appropriately manipulate workpiece 10, as may be required for uniform processing.

Figure 2:
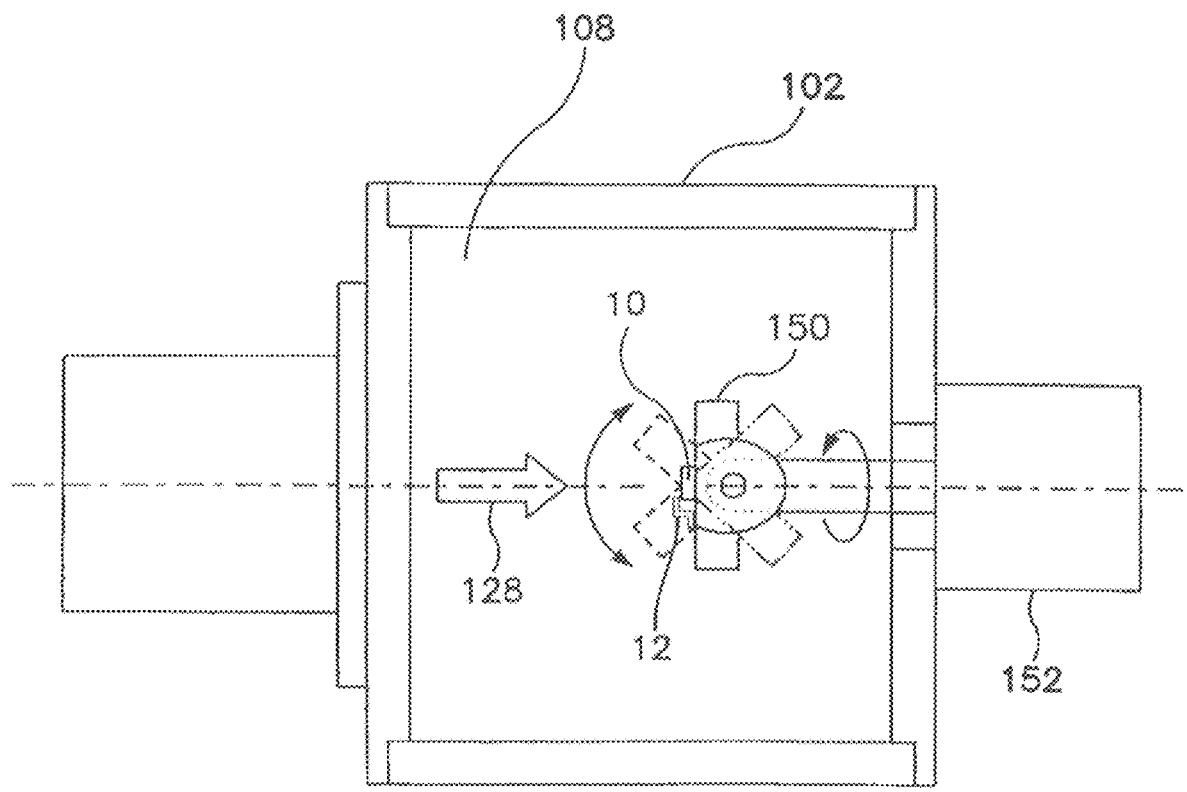
FIG. 2 is an enlarged view of a portion of the gas cluster ion beam processing system showing the workpiece holder.

Referring also to FIG. 2, any workpiece surfaces that are non-planar, that is may be of a spherical or cup-like, rounded, irregular, or other un-flat configuration (as may be encountered among biological materials), may be oriented within a range of angles with respect to the beam incidence to obtain optimal GCIB processing of the workpiece surfaces. This employs a workpiece holder 150 with the ability to be fully articulated for orienting all non-planar surfaces to be processed in suitable alignment with the GCIB to provide processing optimization and uniformity. More specifically, when the workpiece 10 being processed is non-planar, the workpiece holder 150 may be rotated and articulated by a mechanism 152 located at the end of the GCIB processor 100. The articulation/rotation mechanism 152 preferably permits 360 degrees of device rotation about longitudinal axis 155 (which may be coaxial with the initial trajectory 154 of the GCIB 128) and sufficient articulation about an axis 157 perpendicular to axis 155 to maintain the workpiece surface to within a desired range of beam incidence.

Under certain conditions, depending upon the size of the workpiece 10, a scanning system may be desirable to produce uniform irradiation of a large workpiece. Although not necessary for GCIB processing, two pairs of orthogonally oriented electrostatic scan plates 130 and 132 may be utilized to produce a raster or other scanning pattern over an extended processing area. When such beam scanning is performed, a scan generator 156 provides X-axis and Y-axis scanning signal voltages to the pairs of scan plates 130 and 132 through lead pairs 158 and 160 respectively. The scanning signal voltages are commonly triangular waves of different frequencies that cause the GCIB 128 to be converted into a scanned GCIB 148, which scans the entire surface of the workpiece 10.

When beam scanning over an extended region is not desired, processing is generally confined to a region that is defined by the diameter of the beam. The diameter of the beam at the surface of the workpiece can be set by selecting the voltages ($V_{L1}$ and/or $V_{L2}$) of one or more lens power supplies (142 and 144 shown for example) to provide the desired beam diameter at the workpiece. Although not specifically shown, in FIGS. 1 and 2, such prior art GCIB processing systems typically employ sensors and circuits for measuring and controlling the GCIB parameters (as for example acceleration potential, beam current, beam focus, gas flow, beam dose applied to the workpiece, workpiece manipulation, etc.) important to processing and also employ additional controls and automation for automatic processing and processing recipe management, selection, and control.

Although FIGS. 1 and 2 show a workpiece holder and manipulator suitable for holding and manipulating certain types of planar and simply shaped non-planar workpieces, it will be understood by those familiar with the prior art that other types of simpler and more complex holders and manipulators are known. For example, U.S. Pat. No. 6,676,989 granted to Kirkpatrick et al. teaches a holder and manipulator optimized for processing tubular or cylindrical workpieces such as vascular stents. Manipulators for exposing multiple surfaces of biological materials to GCIB or Neutral Beam irradiation will be known to those skilled in the art and/or may readily be constructed using no more than ordinary skill. In an embodiment of the invention, a neutral beam derived from an accelerated gas cluster ion beam is employed to process biological materials.

An Accelerated Low Energy Neutral Beam Derived from an Accelerated GCIB

Figure 3:
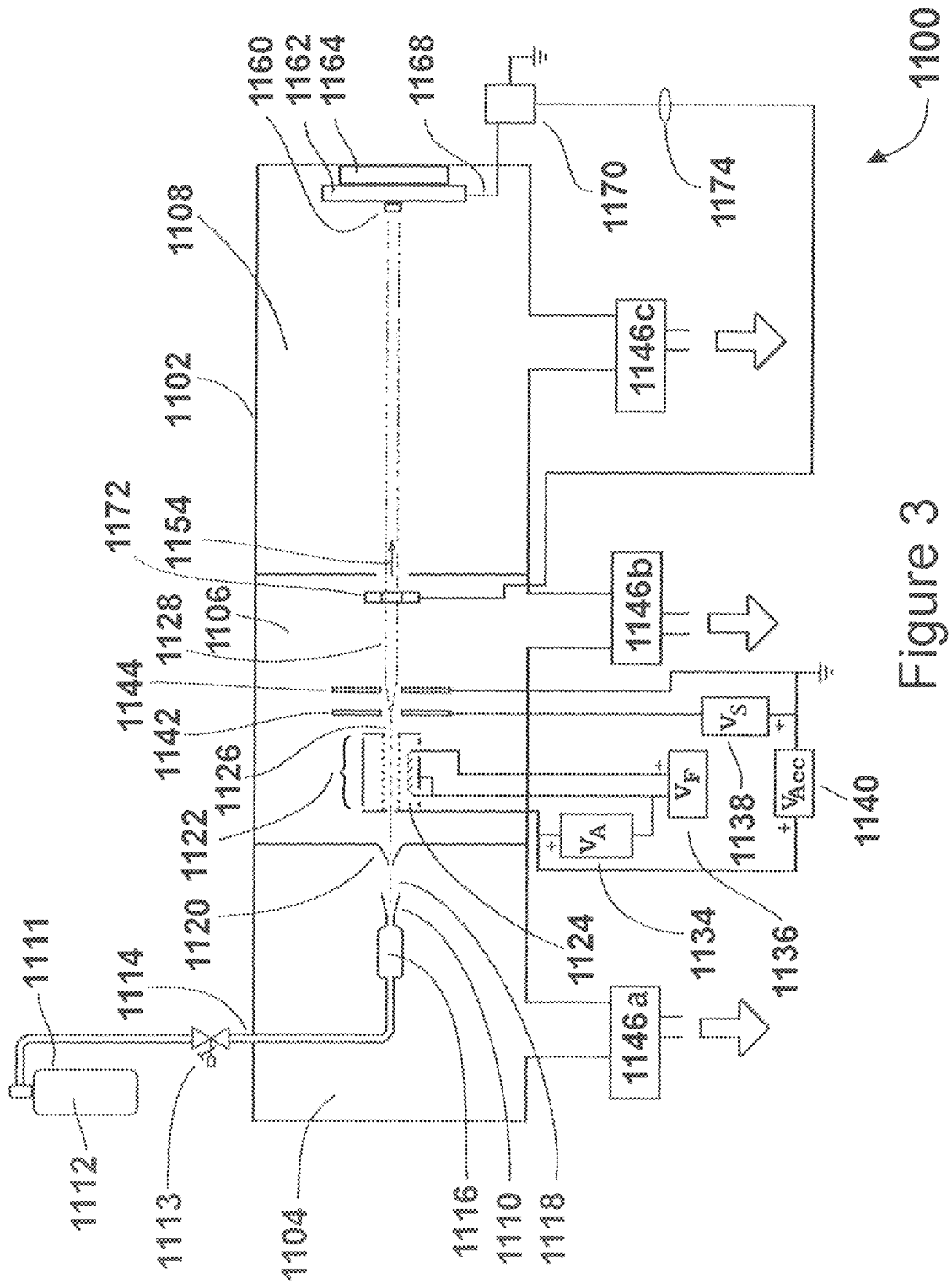
FIG. 3 is a schematic illustrating elements of a prior art GCIB processing apparatus 1100 for processing a workpiece using a GCIB.

FIG. 3, which shows a schematic configuration for a prior art GCIB processing apparatus 1100. A low-pressure vessel 1102 has three fluidly connected chambers: a nozzle chamber 1104, an ionization/acceleration chamber 1106, and a processing chamber 1108. The three chambers are evacuated by vacuum pumps 1146a, 1146b, and 1146c, respectively. A pressurized condensable source gas 1112 (for example argon) stored in a gas storage cylinder 1111 flows through a gas metering valve 1113 and a feed tube 1114 into a stagnation chamber 1116. Pressure (typically a few atmospheres) in the stagnation chamber 1116 results in ejection of gas into the substantially lower pressure vacuum through a nozzle 1110, resulting in formation of a supersonic gas jet 1118. Cooling, resulting from the expansion in the jet, causes a portion of the gas jet 1118 to condense into clusters, each consisting of from several to several thousand weakly bound atoms or molecules. A gas skimmer aperture 1120 is employed to control flow of gas into the downstream chambers by partially separating gas molecules that have not condensed into a cluster jet from the cluster jet. Excessive pressure in the downstream chambers can be detrimental by interfering with the transport of gas cluster ions and by interfering with management of the high voltages that may be employed for beam formation and transport. Suitable condensable source gases 1112 include, but are not limited to argon and other condensable noble gases, nitrogen, carbon dioxide, oxygen, and many other gases and/or gas mixtures. After formation of the gas clusters in the supersonic gas jet 1118, at least a portion of the gas clusters are ionized in an ionizer 1122 that is typically an electron impact ionizer that produces electrons by thermal emission from one or more incandescent filaments 1124 (or from other suitable electron sources) and accelerates and directs the electrons, enabling them to collide with gas clusters in the gas jet 1118. Electron impacts with gas clusters eject electrons from some portion of the gas clusters, causing those clusters to become positively ionized. Some clusters may have more than one electron ejected and may become multiply ionized. Control of the number of electrons and their energies after acceleration typically influences the number of ionizations that may occur and the ratio between multiple and single ionizations of the gas clusters. A suppressor electrode 1142, and grounded electrode 1144 extract the cluster ions from the ionizer exit aperture 1126, accelerate them to a desired energy (typically with acceleration potentials of from several hundred V to several tens of kV), and focuses them to form a GCIB 1128. The region that the GCIB 1128 traverses between the ionizer exit aperture 126 and the suppressor electrode 1142 is referred to as the extraction region. The axis (determined at the nozzle 1110), of the supersonic gas jet 1118 containing gas clusters is substantially the same as the axis 1154 of the GCIB 1128. Filament power supply 1136 provides filament voltage $V_f$ to heat the ionizer filament 1124. Anode power supply 1134 provides anode voltage $V_A$ to accelerate thermoelectrons emitted from filament 1124 to cause the thermo electrons to irradiate the cluster-containing gas jet 1118 to produce cluster ions. A suppression power supply 1138 supplies suppression voltage $V_S$ (on the order of several hundred to a few thousand volts) to bias suppressor electrode 1142. Accelerator power supply 1140 supplies acceleration voltage $V_{Acc}$ to bias the ionizer 1122 with respect to suppressor electrode 1142 and grounded electrode 1144 so as to result in a total GCIB acceleration potential equal to $V_{Acc}$. Suppressor electrode 1142 serves to extract ions from the ionizer exit aperture 1126 of ionizer 1122 and to prevent undesired electrons from entering the ionizer 1122 from downstream, and to form a focused GCIB 1128.

A workpiece 1160, which may (for example) be a medical device, a semiconductor material, an optical element, or other workpiece to be processed by GCIB processing, is held on a workpiece holder 1162, which disposes the workpiece in the path of the GCIB 1128. The workpiece holder is attached to but electrically insulated from the processing chamber 1108 by an electrical insulator 1164. Thus, GCIB 1128 striking the workpiece 1160 and the workpiece holder 1162 flows through an electrical lead 1168 to a dose processor 1170. A beam gate 1172 controls transmission of the GCIB 1128 along axis 1154 to the workpiece 1160. The beam gate 1172 typically has an open state and as closed state that is controlled by a linkage 1174 that may be (for example) electrical, mechanical, or electromechanical. Dose processor 1170 controls the open/closed state of the beam gate 1172 to manage the GCIB dose received by the workpiece 1160 and the workpiece holder 1162. In operation, the dose processor 1170 opens the beam gate 1172 to initiate GCIB irradiation of the workpiece 1160. Dose processor 1170 typically integrates GCIB electrical current arriving at the workpiece 1160 and workpiece holder 1162 to calculate an accumulated GCIB irradiation dose. At a predetermined dose, the dose processor 1170 closes the beam gate 1172, terminating processing when the predetermined dose has been achieved.

Figure 4:
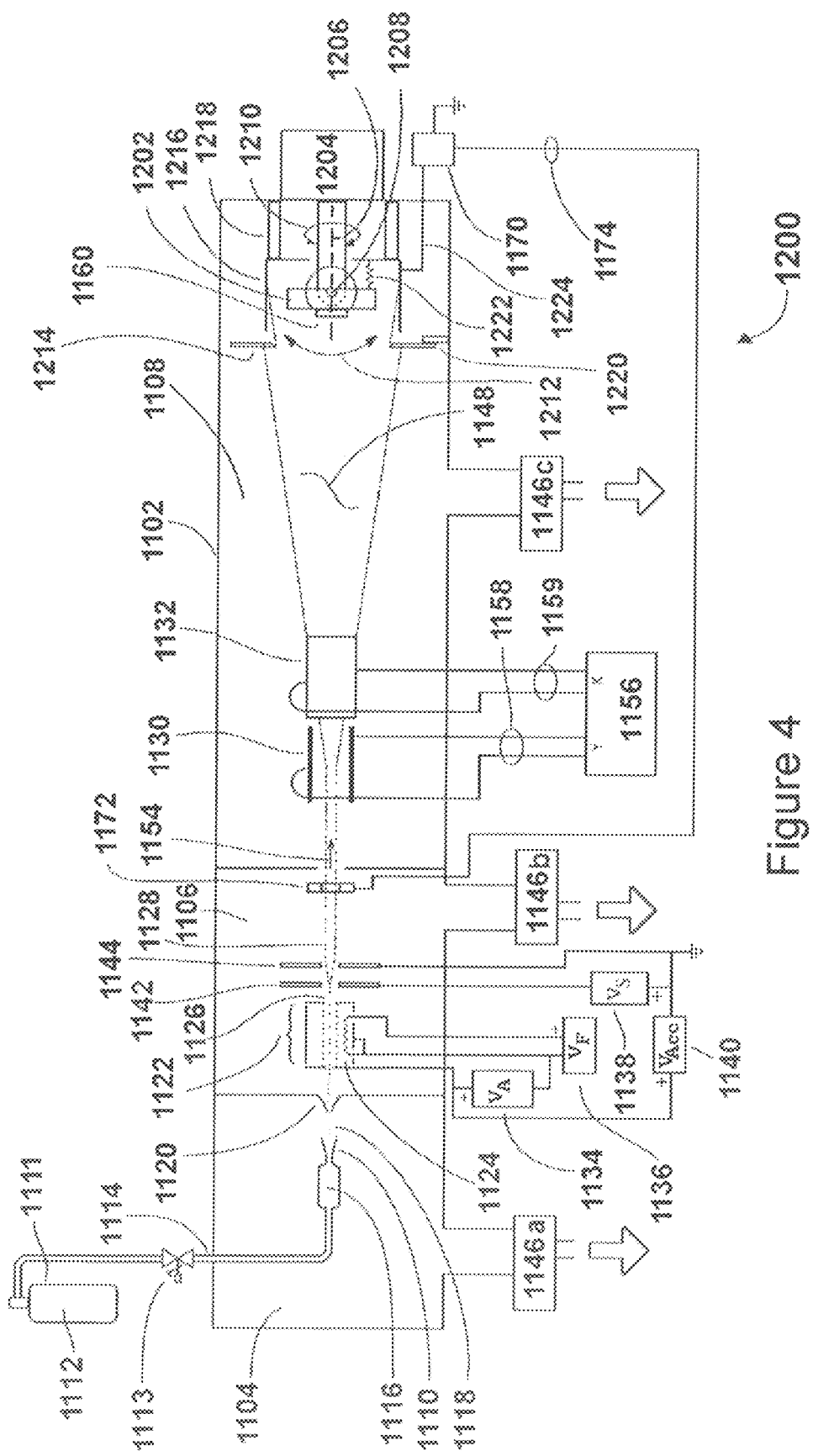
FIG. 4 is a schematic illustrating elements of another prior art GCIB processing apparatus 1200 for workpiece processing using a GCIB, wherein scanning of the ion beam and manipulation of the workpiece is employed.

FIG. 4 shows a schematic illustrating elements of another prior art GCIB processing apparatus 1200 for workpiece processing using a GCIB, wherein scanning of the ion beam and manipulation of the workpiece is employed. A workpiece 1160 to be processed by the GCIB processing apparatus 1200 is held on a workpiece holder 1202, disposed in the path of the GCIB 1128. In order to accomplish uniform processing of the workpiece 1160, the workpiece holder 1202 is designed to manipulate workpiece 1160, as may be required for uniform processing.

Any workpiece surfaces that are non-planar, for example, spherical or cup-like, rounded, irregular, or other un-flat configuration, may be oriented within a range of angles with respect to the beam incidence to obtain optimal GCIB processing of the workpiece surfaces. The workpiece holder 1202 can be fully articulated for orienting all non-planar surfaces to be processed in suitable alignment with the GCIB 1128 to provide processing optimization and uniformity. More specifically, when the workpiece 1160 being processed is non-planar, the workpiece holder 1202 may be rotated in a rotary motion 1210 and articulated in articulation motion 1212 by an articulation/rotation mechanism 1204. The articulation/rotation mechanism 1204 may permit 360 degrees of device rotation about longitudinal axis 1206 (which is coaxial with the axis 1154 of the GCIB 1128) and sufficient articulation about an axis 1208 perpendicular to axis 1206 to maintain the workpiece surface to within a desired range of beam incidence.

Under certain conditions, depending upon the size of the workpiece 1160, a scanning system may be desirable to produce uniform irradiation of a large workpiece. Although often not necessary for GCIB processing, two pairs of orthogonally oriented electrostatic scan plates 1130 and 1132 may be utilized to produce a raster or other scanning pattern over an extended processing area. When such beam scanning is performed, a scan generator 1156 provides X-axis scanning signal voltages to the pair of scan plates 1132 through lead pair 1159 and Y-axis scanning signal voltages to the pair of scan plates 1130 through lead pair 1158. The scanning signal voltages are commonly triangular waves of different frequencies that cause the GCIB 1128 to be converted into a scanned GCIB 1148, which scans the entire surface of the workpiece 1160. A scanned beam-defining aperture 1214 defines a scanned area. The scanned beam-defining aperture 1214 is electrically conductive and is electrically connected to the low-pressure vessel 1102 wall and supported by support member 1220. The workpiece holder 1202 is electrically connected via a flexible electrical lead 1222 to a faraday cup 1216 that surrounds the workpiece 1160 and the workpiece holder 1202 and collects all the current passing through the defining aperture 1214. The workpiece holder 1202 is electrically isolated from the articulation/rotation mechanism 1204 and the faraday cup 1216 is electrically isolated from and mounted to the low-pressure vessel 1102 by insulators 1218. Accordingly, all current from the scanned GCIB 1148, which passes through the scanned beam-defining aperture 1214 is collected in the faraday cup 1216 and flows through electrical lead 1224 to the dose processor 1170. In operation, the dose processor 1170 opens the beam gate 1172 to initiate GCIB irradiation of the workpiece 1160. The dose processor 1170 typically integrates GCIB electrical current arriving at the workpiece 1160 and workpiece holder 1202 and faraday cup 1216 to calculate an accumulated GCIB irradiation dose per unit area. At a predetermined dose, the dose processor 1170 closes the beam gate 1172, terminating processing when the predetermined dose has been achieved. During the accumulation of the predetermined dose, the workpiece 1160 may be manipulated by the articulation/rotation mechanism 1204 to ensure processing of all desired surfaces.

Figure 5:
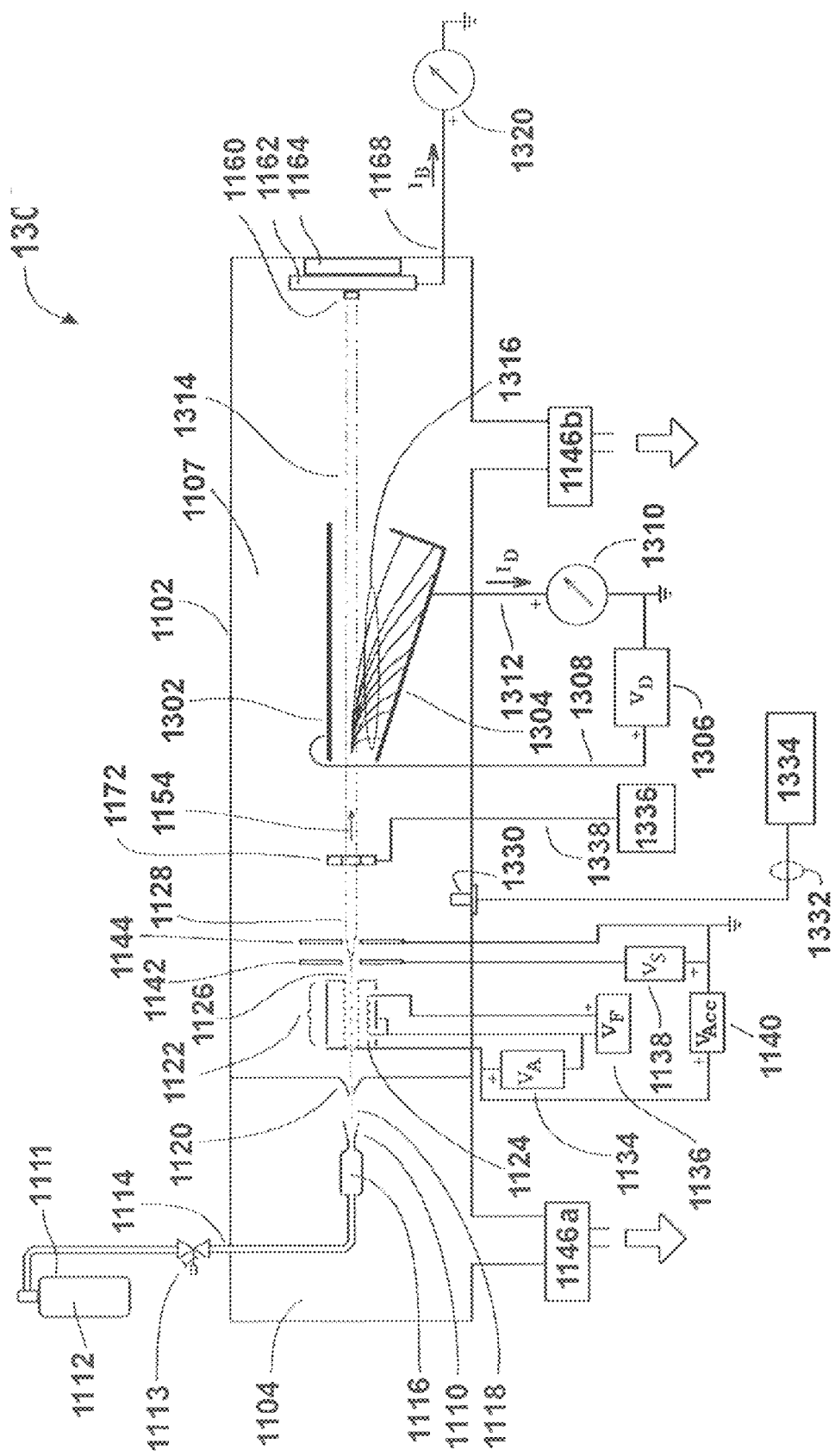
FIG. 5 is a schematic of a Neutral Beam processing apparatus 1300 according to an embodiment of the invention, which uses electrostatic deflection plates to separate the charged and uncharged beams.

FIG. 5 is a schematic of a Neutral Beam processing apparatus 1300 of an exemplary type that may be employed for Neutral Beam processing according to embodiments of the invention. It uses electrostatic deflection plates to separate the charged and uncharged portions of a GCIB. A beamline chamber 1107 encloses the ionizer and accelerator regions and the workpiece processing regions. The beamline chamber 1107 has high conductance and so the pressure is substantially uniform throughout. A vacuum pump 1146b evacuates the beamline chamber 1107. Gas flows into the beamline chamber 1107 in the form of clustered and unclustered gas transported by the gas jet 1118 and in the form of additional unclustered gas that leaks through the gas skimmer aperture 1120. A pressure sensor 1330 transmits pressure data from the beamline chamber 1107 through an electrical cable 1332 to a pressure sensor controller 1334, which measures and displays pressure in the beamline chamber 1107. The pressure in the beamline chamber 1107 depends on the balance of gas flow into the beamline chamber 1107 and the pumping speed of the vacuum pump 1146b. By selection of the diameter of the gas skimmer aperture 1120, the flow of source gas 1112 through the nozzle 1110, and the pumping speed of the vacuum pump 1146b, the pressure in the beamline chamber 1107 equilibrates at a pressure, $P_B$, determined by design and by nozzle flow. The beam flight path from grounded electrode 1144 to workpiece holder 162, is for example, 100 cm. By design and adjustment $P_B$ may be approximately $6\times10^{-5}$ torr ($8\times10^{-3}$ pascal). Thus the product of pressure and beam path length is approximately $6\times10^{-3}$ torr-cm (0.8 pascal-cm) and the gas target thickness for the beam is approximately $1.94\times10^{14}$ gas molecules per cm$^2$, which is observed to be effective for dissociating the gas cluster ions in the GCIB 1128. $V_{Acc}$ may be for example 30 kV and the GCIB 1128 is accelerated by that potential. A pair of deflection plates (1302 and 1304) is disposed about the axis 1154 of the GCIB 1128. A deflector power supply 1306 provides a positive deflection voltage $V_D$ to deflection plate 1302 via electrical lead 1308. Deflection plate 1304 is connected to electrical ground by electrical lead 1312 and through current sensor/display 1310. Deflector power supply 1306 is manually controllable. $V_D$ may be adjusted from zero to a voltage sufficient to completely deflect the ionized portion 1316 of the GCIB 1128 onto the deflection plate 1304 (for example a few thousand volts). When the ionized portion 1316 of the GCIB 1128 is deflected onto the deflection plate 1304, the resulting current, $I_D$ flows through electrical lead 1312 and current sensor/display 1310 for indication. When $V_D$ is zero, the GCIB 1128 is undeflected and travels to the workpiece 1160 and the workpiece holder 1162. The GCIB beam current $I_B$ is collected on the workpiece 1160 and the workpiece holder 1162 and flows through electrical lead 1168 and current sensor/display 1320 to electrical ground. $I_B$ is indicated on the current sensor/display 1320. A beam gate 1172 is controlled through a linkage 1338 by beam gate controller 1336. Beam gate controller 1336 may be manual or may be electrically or mechanically timed by a preset value to open the beam gate 1172 for a predetermined interval. In use, $V_D$ is set to zero, the beam current, $I_B$, striking the workpiece holder is measured. Based on previous experience for a given GCIB process recipe, an initial irradiation time for a given process is determined based on the measured current, $I_B$. $V_D$ is increased until all measured beam current is transferred from $I_B$ to $I_D$ and $I_D$ no longer increases with increasing $V_D$. At this point a Neutral Beam 1314 comprising energetic dissociated components of the initial GCIB 1128 irradiates the workpiece holder 1162. The beam gate 1172 is then closed and the workpiece 1160 placed onto the workpiece holder 1162 by conventional workpiece loading means (not shown). The beam gate 1172 is opened for the predetermined initial radiation time. After the irradiation interval, the workpiece may be examined and the processing time adjusted as necessary to calibrate the duration of Neutral Beam processing based on the measured GCIB beam current $I_B$. Following such a calibration process, additional workpieces may be processed using the calibrated exposure duration.

The Neutral Beam 1314 contains a repeatable fraction of the initial energy of the accelerated GCIB 1128. The remaining ionized portion 1316 of the original GCIB 1128 has been removed from the Neutral Beam 1314 and is collected by the grounded deflection plate 1304. The ionized portion 1316 that is removed from the Neutral Beam 1314 may include monomer ions and gas cluster ions including intermediate size gas cluster ions. Because of the monomer evaporation mechanisms due to cluster heating during the ionization process, intra-beam collisions, background gas collisions, and other causes (all of which result in erosion of clusters) the Neutral Beam substantially consists of neutral monomers, while the separated charged particles are predominately cluster ions. The inventors have confirmed this by suitable measurements that include re-ionizing the neutral beam and measuring the charge to mass ratio of the resulting ions.

Figure 6:
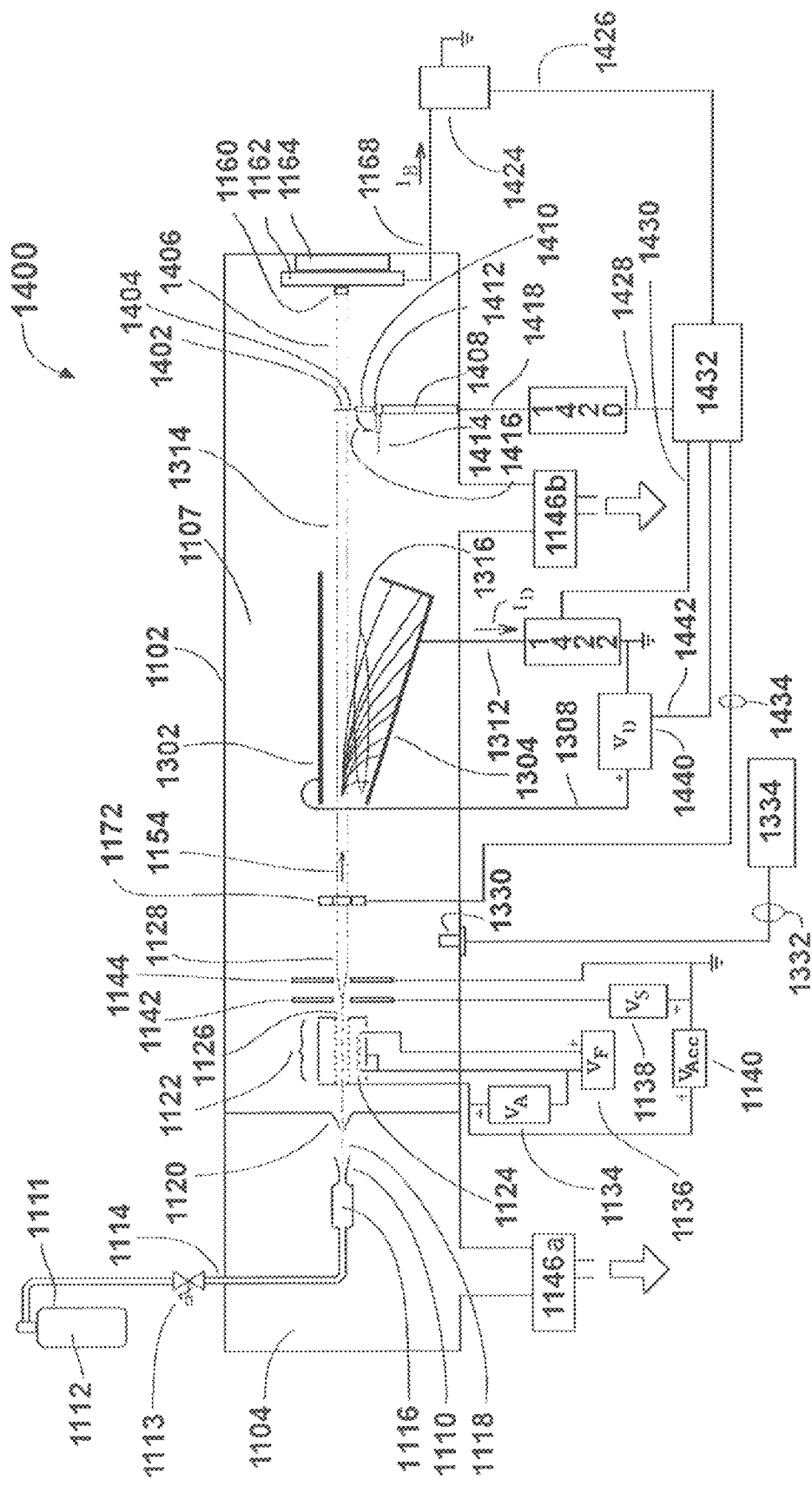
FIG. 6 is a schematic of a Neutral Beam processing apparatus 1400 according to an embodiment of the invention, using a thermal sensor for Neutral Beam measurement.

FIG. 6 is a schematic of a Neutral Beam processing apparatus 1400 as may, for example, be used in generating Neutral Beams as may be employed in embodiments of the invention. It uses a thermal sensor for Neutral Beam measurement. A thermal sensor 1402 attaches via low thermal conductivity attachment 1404 to a rotating support arm 1410 attached to a pivot 1412. Actuator 1408 moves thermal sensor 1402 via a reversible rotary motion 1416 between positions that intercept the Neutral Beam 1314 or GCIB 1128 and a parked position indicated by 1414 where the thermal sensor 1402 does not intercept any beam. When thermal sensor 1402 is in the parked position (indicated by 1414) the GCIB 1128 or Neutral Beam 1314 continues along path 1406 for irradiation of the workpiece 1160 and/or workpiece holder 1162. A thermal sensor controller 1420 controls positioning of the thermal sensor 1402 and performs processing of the signal generated by thermal sensor 1402. Thermal sensor 1402 communicates with the thermal sensor controller 1420 through an electrical cable 1418. Thermal sensor controller 1420 communicates with a dosimetry controller 1432 through an electrical cable 1428. A beam current measurement device 1424 measures beam current $I_B$ flowing in electrical lead 1168 when the GCIB 1128 strikes the workpiece 1160 and/or the workpiece holder 1162. Beam current measurement device 1424 communicates a beam current measurement signal to dosimetry controller 1432 via electrical cable 1426. Dosimetry controller 1432 controls setting of open and closed states for beam gate 1172 by control signals transmitted via linkage 1434. Dosimetry controller 1432 controls deflector power supply 1440 via electrical cable 1442 and can control the deflection voltage $V_D$ between voltages of zero and a positive voltage adequate to completely deflect the ionized portion 1316 of the GCIB 1128 to the deflection plate 1304. When the ionized portion 1316 of the GCIB 1128 strikes deflection plate 1304, the resulting current $I_D$ is measured by current sensor 1422 and communicated to the dosimetry controller 1432 via electrical cable 1430. In operation dosimetry controller 1432 sets the thermal sensor 1402 to the parked position 1414, opens beam gate 1172, sets $V_D$ to zero so that the full GCIB 1128 strikes the workpiece holder 1162 and/or workpiece 1160. The dosimetry controller 1432 records the beam current $I_B$ transmitted from beam current measurement device 1424. The dosimetry controller 1432 then moves the thermal sensor 1402 from the parked position 1414 to intercept the GCIB 1128 by commands relayed through thermal sensor controller 1420. Thermal sensor controller 1420 measures the beam energy flux of GCIB 1128 by calculation based on the heat capacity of the sensor and measured rate of temperature rise of the thermal sensor 1402 as its temperature rises through a predetermined measurement temperature (for example 70 degrees C.) and communicates the calculated beam energy flux to the dosimetry controller 1432 which then calculates a calibration of the beam energy flux as measured by the thermal sensor 1402 and the corresponding beam current measured by the beam current measurement device 1424. The dosimetry controller 1432 then parks the thermal sensor 1402 at parked position 1414, allowing it to cool and commands application of positive $V_D$ to deflection plate 1302 until all of the current $I_D$ due to the ionized portion of the GCIB 1128 is transferred to the deflection plate 1304. The current sensor 1422 measures the corresponding $I_D$ and communicates it to the dosimetry controller 1432. The dosimetry controller also moves the thermal sensor 1402 from parked position 1414 to intercept the Neutral Beam 1314 by commands relayed through thermal sensor controller 420. Thermal sensor controller 420 measures the beam energy flux of the Neutral Beam 1314 using the previously determined calibration factor and the rate of temperature rise of the thermal sensor 1402 as its temperature rises through the predetermined measurement temperature and communicates the Neutral Beam energy flux to the dosimetry controller 1432. The dosimetry controller 1432 calculates a neutral beam fraction, which is the ratio of the thermal measurement of the Neutral Beam 1314 energy flux to the thermal measurement of the full GCIB 1128 energy flux. Under typical operation, a neutral beam fraction of about 50% to about 95% is achieved. Before beginning processing, the dosimetry controller 1432 also measures the current, $I_D$, and determines a current ratio between the initial values of $I_B$ and $I_D$. During processing, the instantaneous $I_D$ measurement multiplied by the initial $I_B/I_D$ ratio may be used as a proxy for continuous measurement of the $I_B$ and employed for dosimetry during control of processing by the dosimetry controller 1432. Thus the dosimetry controller 1432 can compensate any beam fluctuation during workpiece processing, just as if an actual beam current measurement for the full GCIB 1128 were available. The dosimetry controller uses the neutral beam ratio to compute a desired processing time for a particular beam process. During the process, the processing time can be adjusted based on the calibrated measurement of $I_D$ for correction of any beam fluctuation during the process.

Tests were performed to determine the effect of GCIB irradiation on the droplet contact angle (as a measure of hydrophilicity) for biological tissues. Young porcine knees were used to harvest medial collateral ligaments (MCL) and lateral collateral ligaments (LCL) as well as femur shafts. The ligaments were carefully dissected from other loose tissues, rinsed in phosphate buffered saline (PBS) and cut into pieces of approximately 1 cm length by their natural width of approximately 5 mm. Bone shafts were cut to cylinders approximately 2 cm in length and further cut longitudinally down the shaft to semi-circle shaped pieces. The pieces were cleaned of periosteum by pulling it off using forceps and were then rinsed in PBS. Subsequent processing of both the bone and ligament tissue samples (including controls) was identical. Tissues were stored in PBS overnight. Then the tissue samples (both bone and ligament) were removed from PBS and individually introduced into a GCIB processing system's processing chamber. The processing chamber was evacuated to a rough vacuum of approximately 100 mtorr (evacuation time for achieving rough vacuum was approximately 30 minutes for the bone samples and approximately 2 minutes for the ligament samples.) After achieving rough vacuum, the samples were subsequently introduced to high vacuum and exposed to high vacuum (approximately $6 \times 10^{-5}$ torr.) Test samples of both bone and ligament tissues were then treated in high vacuum by GCIB irradiation. Control samples were not irradiated but were subjected to the same vacuum conditions and durations. GCIB irradiation consisted of administering a surface dose of $5 \times 10^{14}$ argon clusters per $cm^2$ at 30 kV acceleration potential to the irradiated surfaces. The irradiation time and corresponding high vacuum exposure duration was approximately 3 minutes and 20 seconds for both the bone and ligament tissue samples.

Following GCIB irradiation and/or vacuum exposure, the tissue samples were allowed to air dry over night in a bio-safety cabinet.

Wettability of the samples was examined by using a Drop Shape Analysis System (Krüss GmbH, Hamburg, Germany, model DSA-10, with Krüss DSA1 version 1.8 analysis software) was used to determine surface contact angles for water droplets on the tissue samples. Identical measurements were made for the bone and ligament tissues, both the irradiated samples and the unirradiated control samples. For each measurement, data was obtained 5 seconds after placing a 3 microliter droplet of deionized water on each of the surfaces (ligament and bone, both irradiated and unirradiated controls.) All measurements were performed under ambient conditions and each analysis was performed in triplicate (three tests on each single sample.)

Results showed an increase of hydrophilicity as measured by decreased contact angle for the ligament and bone samples that were GCIB irradiated, as compared to the unirradiated control samples.

Figure 7:
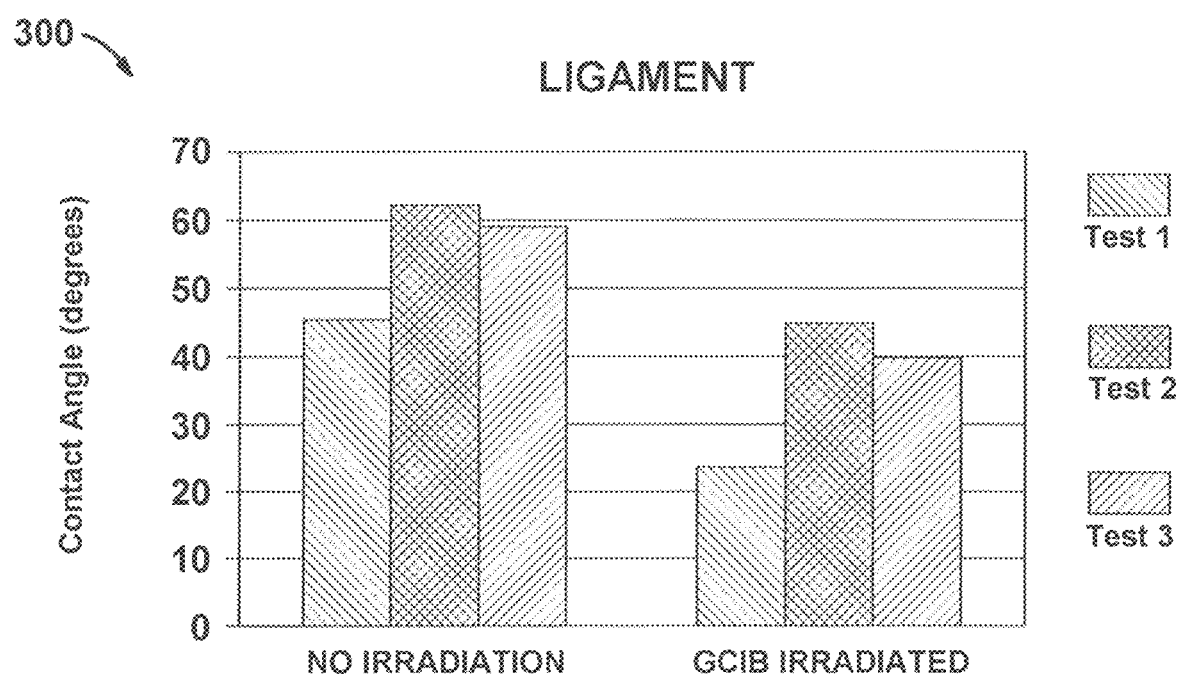
FIG. 7 is a chart 300 showing a measured reduction of droplet contact angle resulting from GCIB irradiation of ligament tissue according to an embodiment of the invention.

FIG. 7 is a chart 300 showing droplet surface contact angle test results for each of three measurements on ligament tissue samples, for both GCIB irradiated and the unirradiated control samples. Droplet contact angle measurements using deionized water on the ligament tissues show an increased hydrophilic surface on the ligament tissue in response to GCIB treatment, Droplet contact angles (in degrees) decreased from an average of 55.59 (standard deviation 9.03) in the unirradiated control ligament to 36.09 (standard deviation 10.93) in the GCIB irradiated samples (statistical significance of the change, $p<0.004$).

Figure 8:
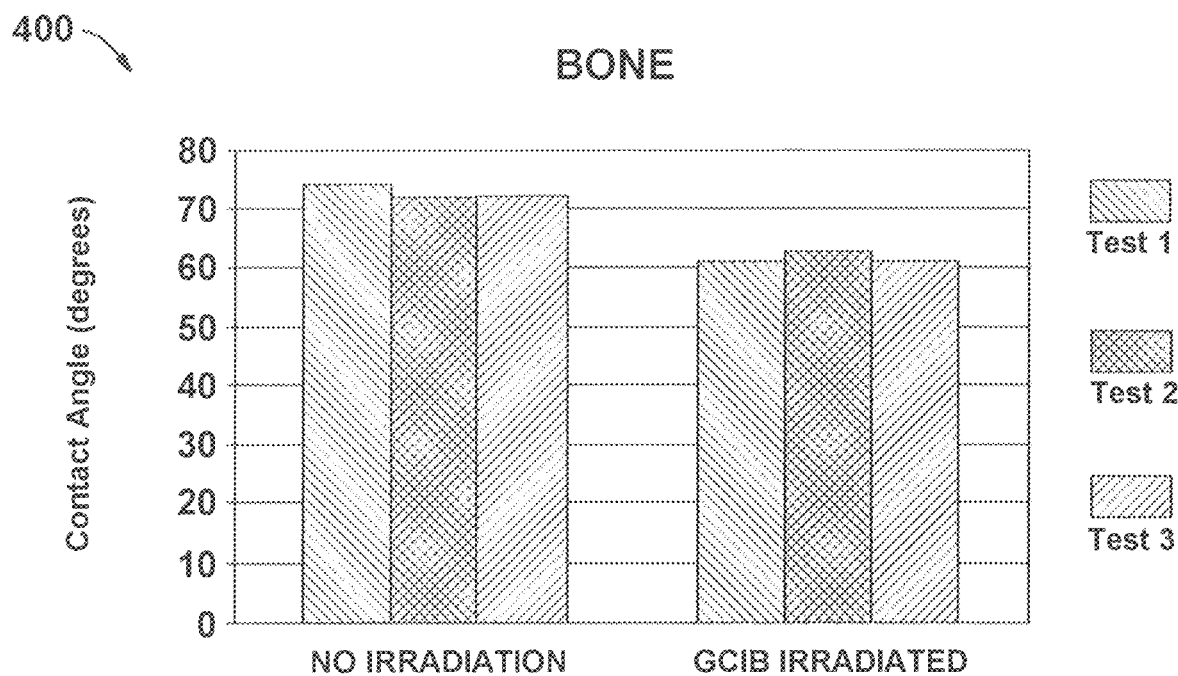
FIG. 8 is a chart 400 showing a measured reduction of droplet contact angle resulting from GCIB irradiation of bone tissue according to an embodiment of the invention.

FIG. 8 is a chart 400 showing droplet surface contact angle test results for each of three measurements on bone tissue samples, for both GCIB irradiated and the unirradiated control samples. Droplet contact angle measurements using deionized water on the bone tissues show an increased hydrophilic surface on the bone tissue in response to GCIB treatment. Droplet contact angles (in degrees) decreased from an average of 72.86 (standard deviation 1.47) in the unirradiated control bone to 61.42 (standard deviation 1.06) in the GCIB irradiated samples (statistical significance of the change, $p<0.015$).

Using an accelerated neutral beam derived from an Argon GCIB accelerated using 30 kV acceleration potential and using an irradiated dose $2.5 \times 10^{17}$ argon atoms per $cm^2$ using 30 kV acceleration potential (thus having the energy equivalence of a dose of $5 \times 10^{14}$ argon cluster ions per $cm^2$ using 30 kV acceleration potential), additional experiments have been performed and show that accelerated Neutral Beams are similarly effective to GCIBs for increasing the hydrophilicity of surfaces (compared to control samples), as determined using surface contact angle measurements for water droplets on the tissue samples. Neutral Beams have an additional property that they do not transport electrical charges to the surfaces they irradiate and are thus less likely to result in subsurface damage.

The tests were performed to determine the effect on bone of Neutral Beam irradiation for changing the droplet contact angle (in degrees, as a measure of hydrophilicity) as follows. Bovine femur was used to harvest marrow-free femur shafts. The bone shafts were cleaned of periosteum by pulling it off using forceps and were then rinsed in PBS. Bone shafts were cut to form 10 mm×10 mm×1 mm pieces. The pieces were cleaned and partially decellularized using the published conventional method of Woods and Gratzner (Woods, T and Gratzner, P. F., "Effectiveness of three extraction techniques in the development of a decellularized bone-anterior cruciate ligament-bone graft", Biomaterials v26, (2005) pp. 7339-7349.) The bone pieces were stored in PBS overnight, lyophilized, and then individually introduced into a Neutral Beam processing system's processing chamber. The processing chamber was evacuated to a rough vacuum of approximately 100 mtorr. After achieving rough vacuum, the samples were subsequently introduced to high vacuum (approximately $6 \times 10^{-5}$ torr.) Test samples of bone were then treated in high vacuum by Neutral Beam irradiation of a surface. Control samples were not irradiated but were subjected to the same vacuum conditions and durations. Neutral Beam irradiation consisted of administering a surface dose to the irradiated surface of $2.5 \times 10^{17}$ argon atoms per $cm^2$ using 30 kV acceleration potential.

Following Neutral Beam irradiation and/or vacuum exposure (controls), the bone samples were tested for wettability. Wettability of the samples was examined by determining surface contact angles for water droplets on the bone samples. Identical measurements were made for the irradiated samples and the unirradiated control samples. For each measurement, data was obtained 5 seconds after placing a 3 microliter droplet of deionized water on the surface. All measurements were performed under ambient conditions and each analysis was performed in quadruplicate (four tests at different locations on each irradiated or control sample).

Figure 9:
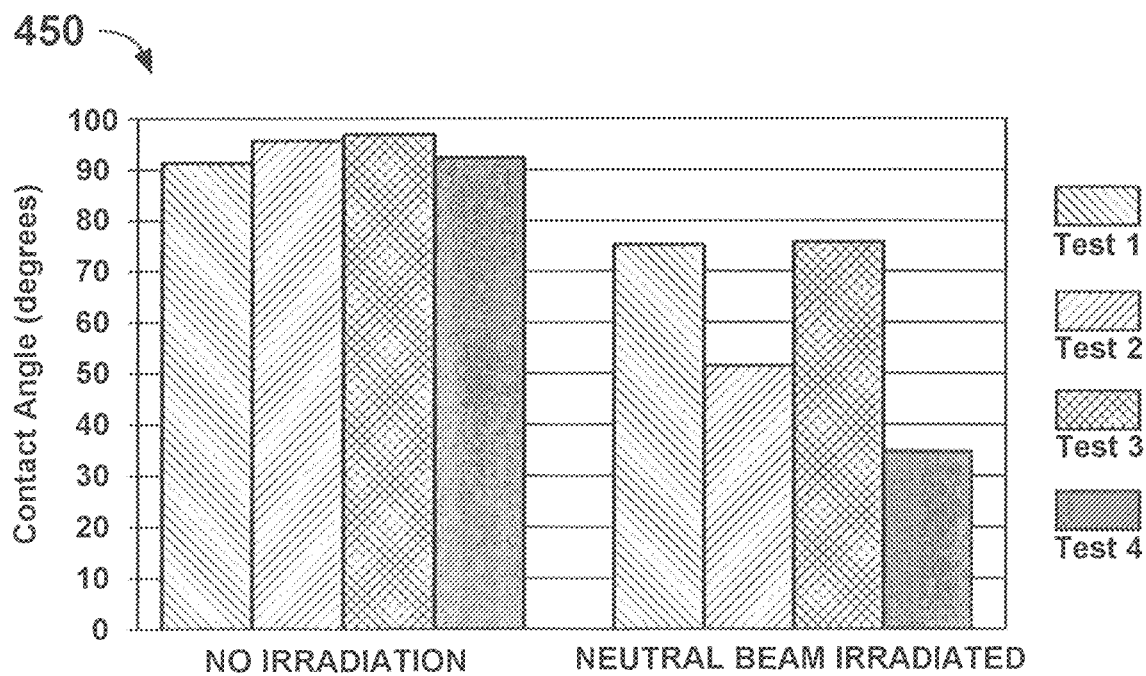
FIG. 9 is a chart 450 showing a measured reduction of droplet contact angle resulting from Neutral Beam irradiation of bone tissue according to an embodiment of the invention.

FIG. 9 is a chart 450 showing droplet surface contact angle test results for each of four measurements on bone tissue samples, for both Neutral Beam irradiated and the unirradiated control samples. Droplet contact angle measurements using deionized water on the bone tissues show an increased hydrophilic surface on the bone tissue in response to Neutral Beam treatment. Droplet contact angles (in degrees) decreased from an average of 94.1 (standard deviation 2.6) in the unirradiated control bone to 59.5 (standard deviation 19.9) in the Neutral Beam irradiated samples (statistical significance of the change, $p<0.038$). It is noted that the Neutral Beam experiment summarized in the chart of FIG. 9, and described above, produced a greater percentage decrease in contact angle than resulted from the GCIB experiment summarized in the chart of FIG. 8, and described above (mean contact angle decrease of 37% for Neutral Beam irradiation compared to 16% for GCIB irradiation.) Because GCIB and/or Neutral Beam treatment of biological surfaces resulted in a more hydrophilic surface, additional tests were done to show that GCIB treatment of decellularized ligaments results in a surface that can be better re-cellularized by (for example) fibroblast cells. Pieces of porcine anterior cruciate ligament (ACL) were used to harvest fibroblasts using a published explant method (Ross S M, Joshi R, and Frank C B; "Establishment and comparison of fibroblast cell lines from the medial collateral and anterior cruciate ligaments of the rabbit" *In Vitro Cell Dev Biol* 1990; 26:579-84.) Freshly isolated LCL and MCL from young porcine knees were then decellularized using the technique of an established method (Woods T, Gratzer P F; "Effectiveness of three extraction techniques in the development of a decellularized bone-anterior cruciate ligament-bone graft", *Biomaterials* 2005, 26:7339-7349.)

Except for GCIB irradiation, subsequent processing of the ligament tissue samples (both the test samples and the controls) was identical. Decellularized tissues were stored in PBS overnight. Then the decellularized tissue samples were removed from PBS and individually introduced into a GCIB processing system's processing chamber. The processing chamber was evacuated to a rough vacuum of approximately 100 mtorr (evacuation time for achieving rough vacuum was approximately 2 minutes for the ligament samples.) After achieving rough vacuum, the samples were subsequently introduced to high vacuum and exposed to high vacuum (approximately $6 \times 10^{-5}$ torr) Test samples of decellularized ligament tissues were then treated in high vacuum by GCIB irradiation. Control samples were not irradiated, but were subjected to the same vacuum conditions and durations. GCIB irradiation consisted of administering a surface dose of $5 \times 10^{14}$ argon clusters per cm$^2$ at 30 kV acceleration potential to the irradiated surfaces. The irradiation time and corresponding high vacuum exposure duration was approximately 3 minutes and 20 seconds for both the decellularized ligament tissue samples (irradiated and control).

Approximately $2 \times 10^5$ fibroblast cells suspended in Sigma E1270 extracellular matrix (ECM) were placed on either side of the ligament samples (to seed the decellularized and irradiated tissue with new cells) and placed in tubes containing appropriate cell growth medium (Dulbecco's Modified Eagle Medium (DMEM)+10% fetal bovine serum (FBS)+1% Penicillin/Streptomycin Antibiotic (supplied by Invitrogen)) and allowed to grow for 18 days with regular medium change every 3 days. Ligament specimens were then fixed in formalin, processed for histology and stained with hematoxylin and eosin. Microscopic inspection of the ligaments revealed a much enhanced cellular attachment and proliferation on the ligament samples receiving GCIB treatment as compared to those controls without GCIB treatment.

FIG. 9 shows a micrograph 500 showing a surface region 502 of an unirradiated control sample of decellularized porcine ligament tissue 504 processed as described above including vacuum exposure, but without GCIB irradiation. A 1- to 2-cell layer 506 of newly grown fibroblast cells is seen attached to the underlying ligament tissue 504.

Figure 10:
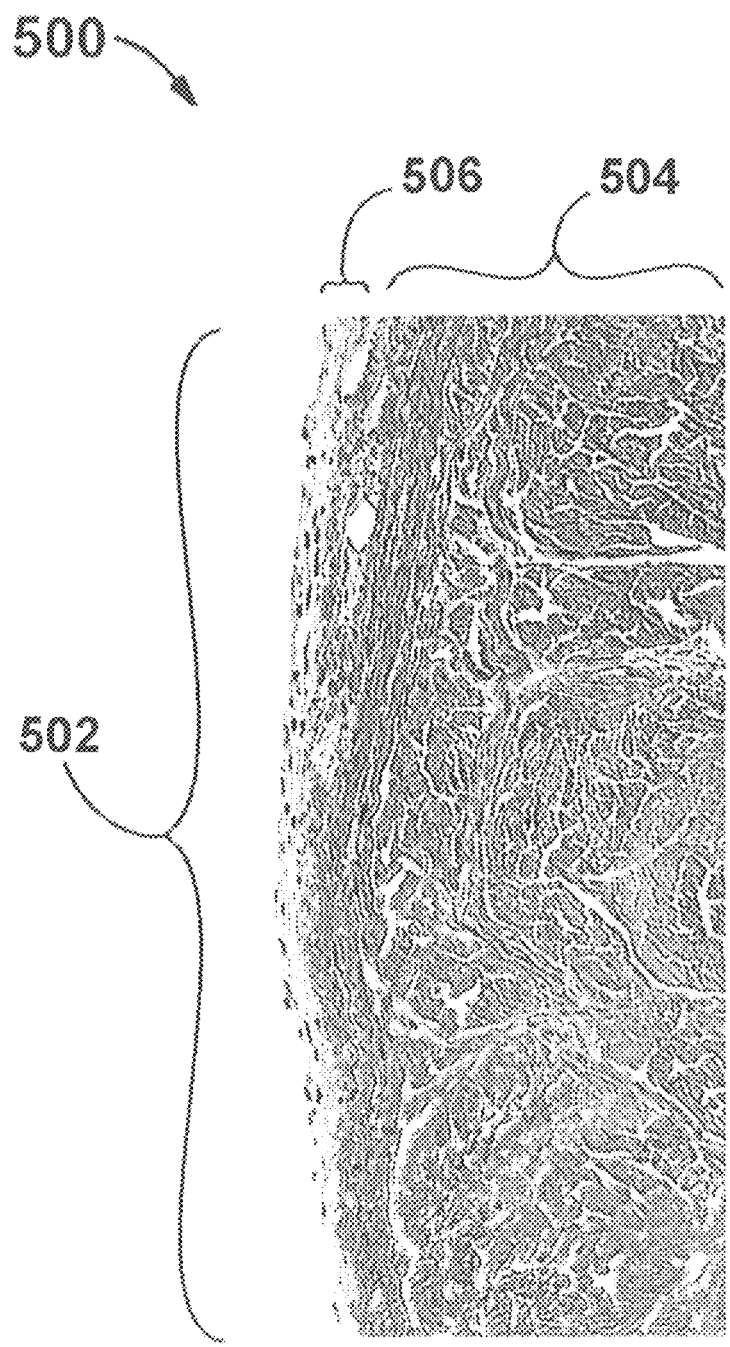
FIG. 10 is a micrograph 500 showing cell growth on a control ligament sample.
Figure 11:
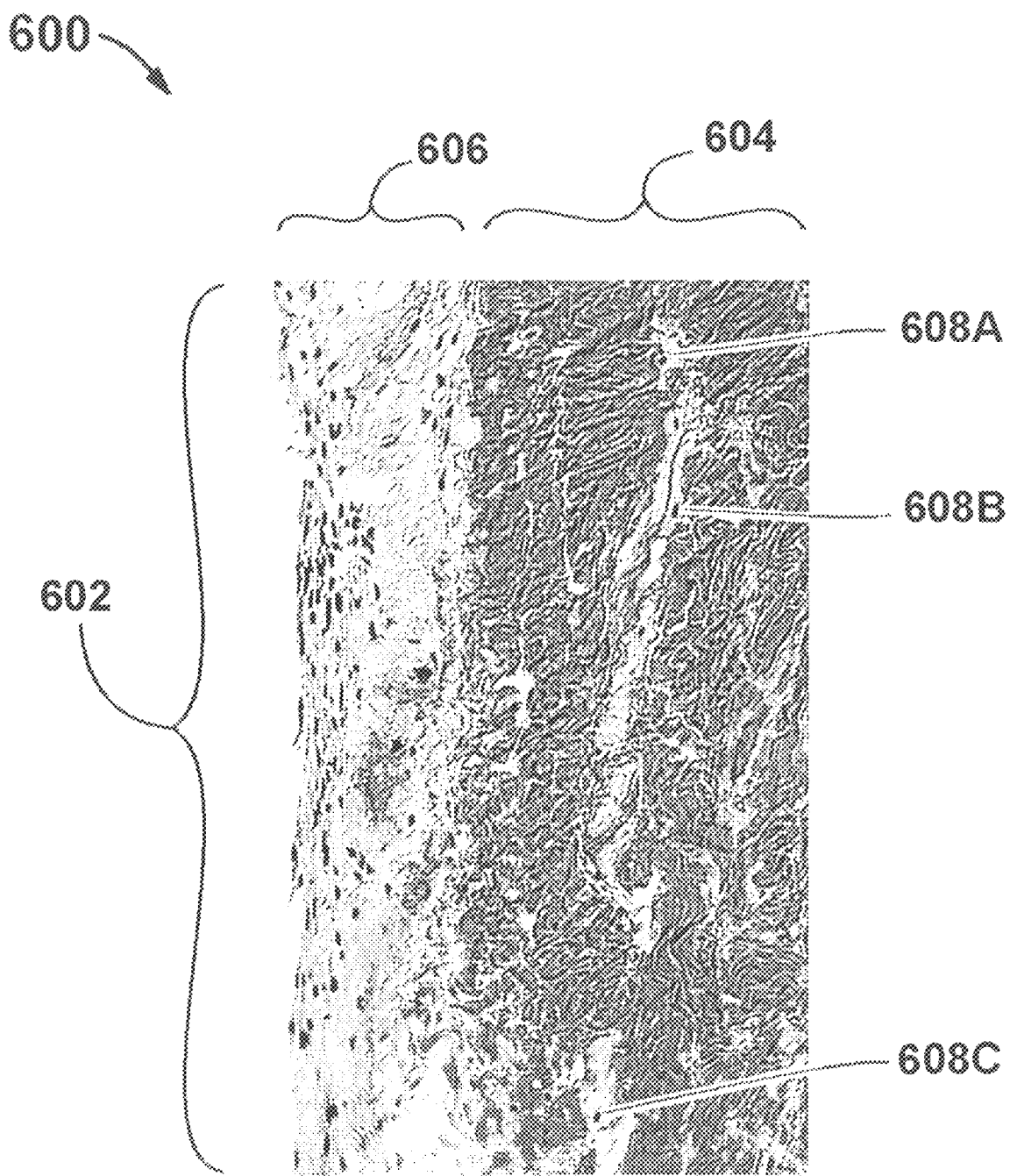
FIG. 11 is a micrograph 600 showing enhanced cell growth on a ligament sample processed according to an embodiment of the invention.

FIG. 10 shows a micrograph 600 showing a surface region 602 of a GCIB irradiated sample of decellularized porcine ligament tissue 604 processed as described above, including both vacuum exposure and GCIB irradiation. Magnification in FIG. 10 is the same as for that in FIG. 9. In FIG. 10, a 3- to 7-cell layer 606 of newly grown fibroblast cells is seen attached to the underlying ligament tissue 604 at the irradiated surface. Furthermore, numerous new fibroblast cells (608A, 608B, and 608C for examples) are seen embedded much deeper into the decellularized ligament tissue. The newly grown fibroblast cells, in addition to having proliferated on the GCIB irradiated surface have begun migrating into the ligament.

These results indicate that the GCIB irradiation of the surface of the decellularized ligament has created a more favorable environment for attachment, growth, or proliferation of the fibroblast cells on the outer surface such that there is more vigorous surface growth and increased migration into the ligament. The migration of cells into the ligament is an important advance in the field of ligament tissue engineering for surgical implant. GCIB or Neutral Beam treatment of biological materials may result in significantly improved clinical outcomes for surgical procedures (as for example an ACL reconstruction). Hitherto, ACL reconstructive surgery (for example) has limited success over time due, in part, to relatively poor integration of transplanted ligament or tendon tissue into the body. GCIB or Neutral Beam treated ligaments or tendons will integrate more rapidly and form a more tightly bound integration that extends the benefits achieved with traditional ACL reconstructive surgical techniques.

In another experiment, further tests were performed to determine the effect of GCIB and Neutral Beam irradiation of bone for promoting cell attachment and proliferation. Decellularized human cadaver bone was used. The pieces were cleaned and partially decellularized using the published conventional method of Woods and Gratzner. The bone pieces were stored in PBS overnight. Then the bone samples were removed from PBS, lyophilized, and cut into 10 mm×6 mm×3 mm pieces. Samples were either irradiated using GCIB or irradiated using Neutral Beam or processed as controls (same processing and handling steps including vacuum treatment, except without irradiation). Irradiated samples were individually introduced into a processing system's processing chamber. The processing chamber was evacuated to a rough vacuum of approximately 100 mtorr. After achieving rough vacuum, the samples were subsequently introduced to high vacuum and exposed to high vacuum (approximately $6 \times 10^{-5}$ torr.) The bone samples were then treated in high vacuum by Neutral Beam or by GCIB irradiation. Control samples were not irradiated but were subjected to the same vacuum conditions and durations. GCIB irradiation samples received a GCIB dose of $5 \times 10^{14}$ argon cluster ions per cm$^2$ using 30 kV acceleration potential and Neutral Beam irradiation consisted of administering a surface dose of $2.5 \times 10^{17}$ argon atoms per cm$^2$ using 30 kV acceleration potential (the Neutral Beam was derived from a GCIB accelerated using 30 kV acceleration potential). These two doses are energetically equivalent doses per cm$^2$.

Following Neutral Beam or GCIB irradiation and/or vacuum exposure (for controls), the bone samples were seeded with living cells.

Approximately 2000 human osteoblast cells suspended in 1 ml of DMEM+10% FBS were seeded onto the 10 mm by 6 mm irradiated or control surface of each of the bone pieces (to seed the decellularized and irradiated bone with new cells) and placed into wells of non-tissue culture treated plates (Becton Dickenson Falcon 351147) containing appropriate cell growth medium (DMEM+10% FBS+1% Penicillin/Streptomycin Antibiotic (supplied by Invitrogen)). The samples were incubated and the cells were allowed to attach and proliferate on the bone sample surfaces for 8 days. The bone pieces with any attached cells were then fixed in formalin, and prepared for examination using scanning electron microscope (SEM) imaging.

Figure 12A:
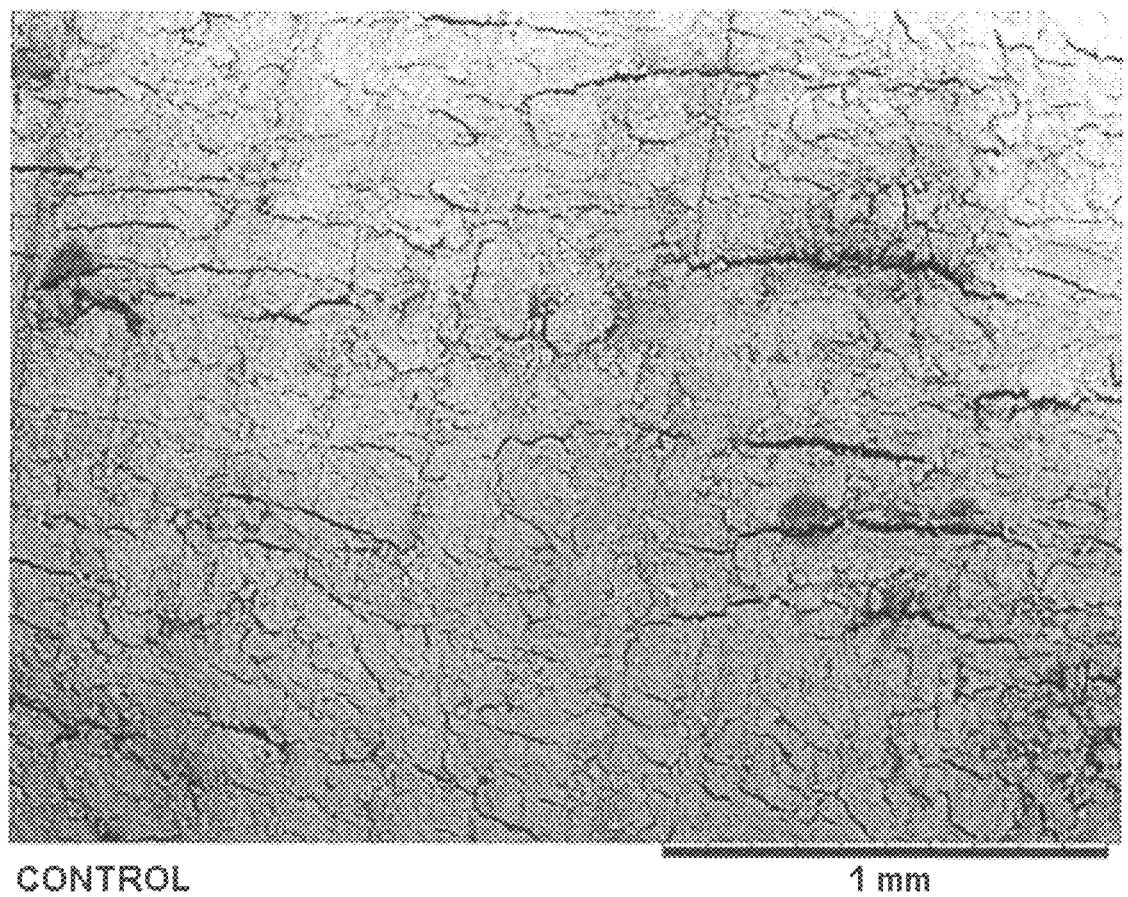
FIGS. 12A, 12B, and 12C are scanning electron microscope images of un-irradiated control, Neutral Beam irradiated, and GCIB irradiated bone samples, illustrating enhanced attachment to and proliferation of cells on the irradiated samples as compared to the control sample.

FIG. 12A is a SEM image of a portion of the un-irradiated bone control sample 8 days after cell seeding. The image shows predominately bone with little osteoblast attachment. For scale a 1 mm marker bar is provided below the image.

Figure 12B:
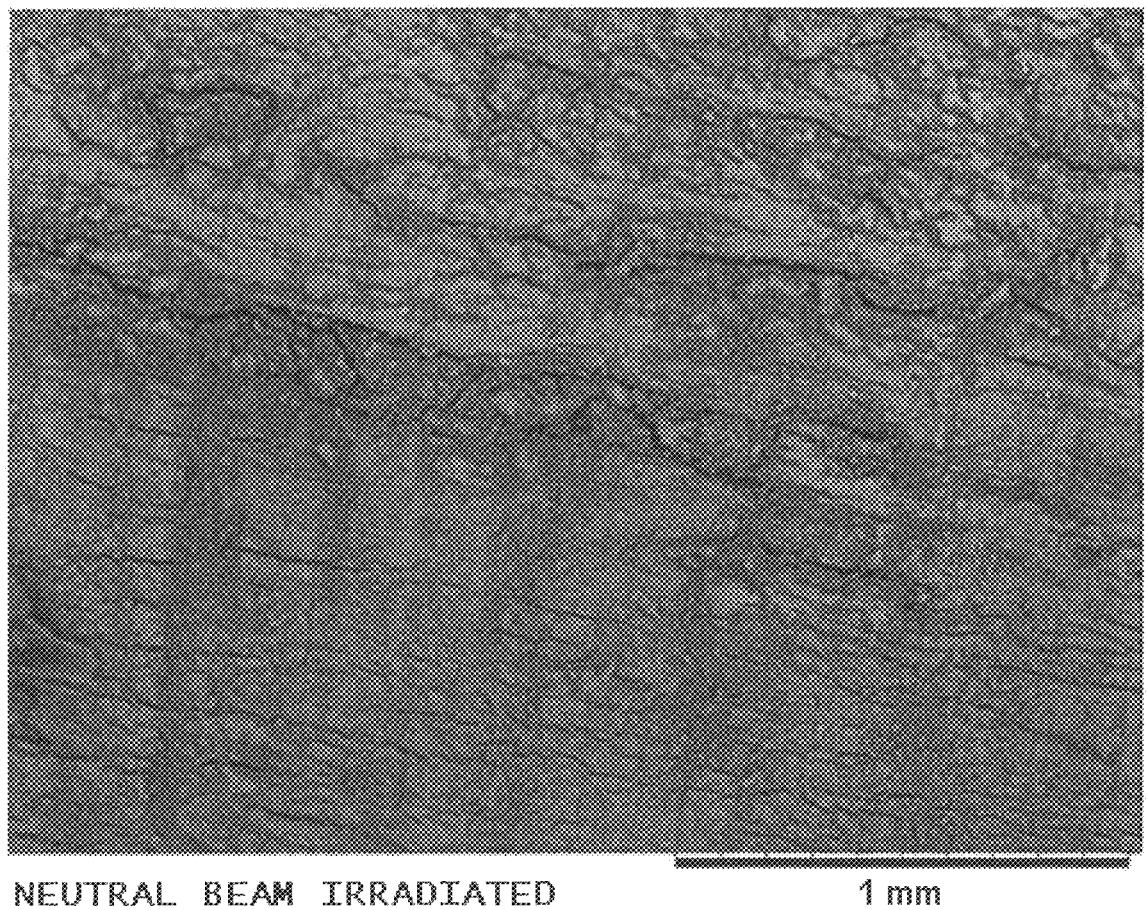

FIG. 12B is a SEM image of a portion of the irradiated surface of the Neutral Beam processed bone sample 8 days after cell seeding.

Figure 12C:
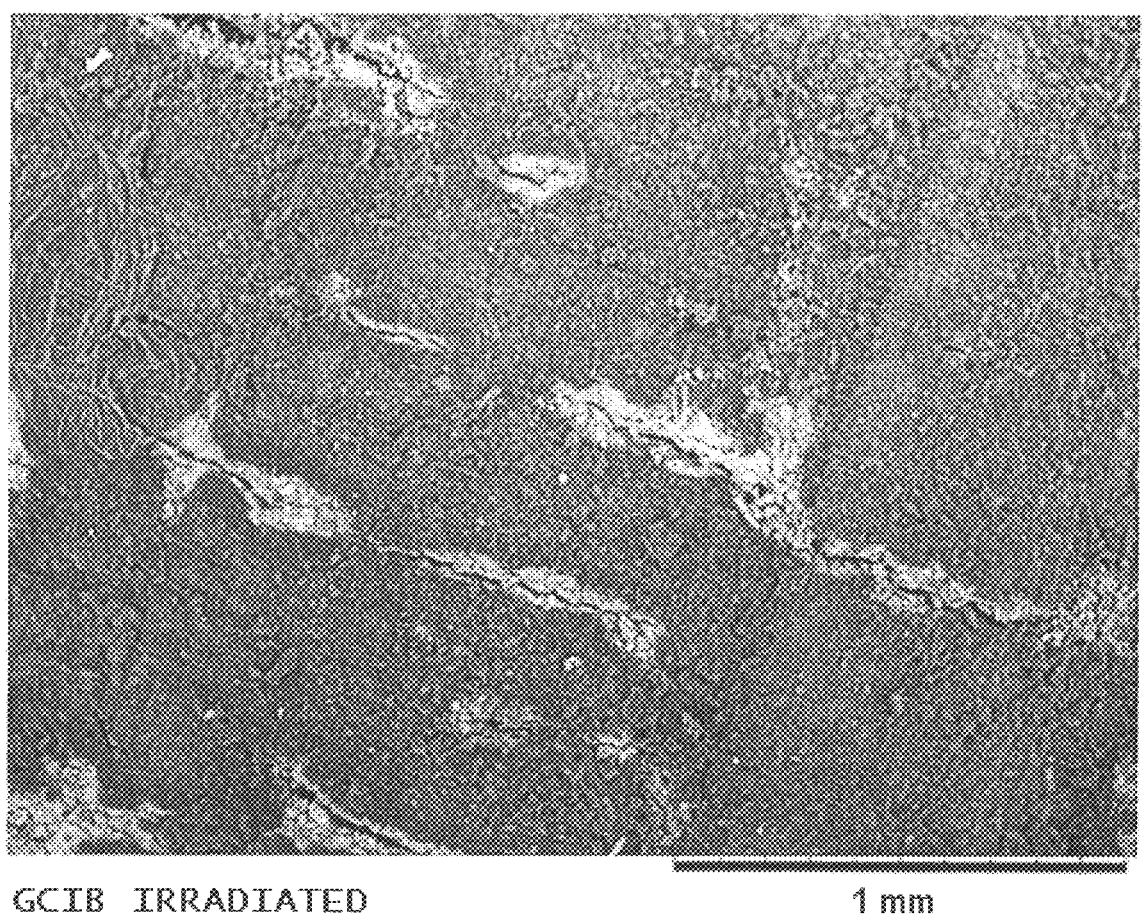

FIG. 12C is a SEM image of a portion of the irradiated surface of the irradiated surface of the GCIB processed bone sample 8 days after cell seeding.

Both the Neutral Beam processed bone sample (FIG. 12B) and the GCIB processed bone sample (FIG. 12C) show nearly complete coverage of the bone surface with an osteoblast cell layer, indicating improved attachment and proliferation on the irradiated samples compared to the un-irradiated control sample (FIG. 12A.)

It is commonly known that primary culture cells de-differentiate while growing in vitro. Various growth and mitogenic factors may be added in culture to maintain the original genotype and morphology of the cells. Primary human osteoblasts were grown in tissue culture plates with no additional growth or mitogenic factors other than found in the (Invitrogen) Dulbecco's Modified Eagle Medium+ 10% fetal bovine serum+1% penicillin/streptomycin antibiotic for two to four passages. Osteoblasts in passage two to four were seeded onto titanium either in control state or that had been irradiated by GCIB at $5 \times 10^{14}$ argon clusters per $cm^2$ and the osteoblasts were allowed to attach and proliferate for 1, 7, or 10 days. Following this time, RNA was extracted from the cells using the TRIzol method (Invitrogen). Following RNA quantification by UV-spectrometry analysis, equal quantities of RNA (1 micro-g) were reverse transcribed into cDNA using the iScript cDNA synthesis kit (Bio-Rad). 100 pg of the resulting cDNA was subjected to real-time polymerase chain reaction (Real Time PCR) for expression analysis of various genes known to be involved in osteogenesis including alkaline phosphatase—liver, bone, kidney (ALPL) known to be involved during bone formation and mineralization, and bone gamma-carboxyglutamate (gla) protein (BGLAP) known to produce a bone protein called Osteocalcin, and corrected for the house keeping gene GAPDH. The analysis was performed on a StepOne system with TaqMan Gene Expression Master Mix and gene specific primers (all from Applied Biosystems), n=3 per condition and time point. The fold change relative to control results were obtained using the $\Delta\Delta C_T$ method. We have shown that osteoblast cells grown on the argon GCIB-treated titanium lead to 3.41 fold increase in ALPL and 2.66 fold increase in BGLAP as compared to non-GCIB-treated titanium at day 10 (statistical significance of the change, $p<0.05$) indicating that the osteoblast cells are undergoing differentiation that will lead towards osteogenesis. Thus the GCIB treatment of a surface, alone, induces differentiation of cells proliferating on the GCIB treated surface.

Using an Neutral Beam derived from an Argon GCIB accelerated using 30 kV acceleration potential and an irradiated dose having the energy equivalence of $5 \times 10^{14}$ argon clusters per $cm^2$, additional experiments have been performed and show that accelerated Neutral Beams are also effective for increasing the attachment and growth of cells on Neutral Beam irradiated surfaces (compared to control samples) Neutral Beams have an additional property that they do not transport electrical charges to the surfaces they irradiate and thus avoid charge-induced damage or other degradation of the surfaces.

In the case of biological materials, it is often desirable that only preselected portions of the materials should be processed by GCIB or Neutral Beam irradiation, while other portions are best not irradiated. In such situations, controlling the GCIB or Neutral Beam cross-sectional area and controlling the scanning and/or deflecting of the GCIB or Neutral Beam to limit the extent of its irradiation to only the desired areas may control exposure of selected portions of the biological materials to GCIB or Neutral Beam. Alternatively, conventional masking technology may be used to control the mask surface areas of the biological materials for which irradiation is not desired, and to expose surface areas for which irradiation is desired. Subsequently the mask and the biological material exposed through the mask are irradiated with a diffuse or scanned GCIB or Neutral Beam. Various other methods of limiting the GCIB or Neutral Beam irradiation to selected regions of a biological material will be known to those skilled in the art and are intended to be encompassed in the invention.

Certain first selected portions of a biological material may be processed performing a first GCIB or Neutral Beam irradiation upon those selected portions. Additional selected portions of the biological material may further be processed by performing one or more additional processes of GCIB or Neutral Beam irradiation. The additional GCIB or Neutral Beam irradiation process(es) may employ different GCIB or Neutral Beam and vacuum processing conditions, for example different GCIB or Neutral Beam doses, or different constituent gases in the gas cluster ions, or different beam acceleration potentials (resulting in different ion beam energy and velocity). The additional selected portions may be different portions from the first selected portions or may partially or completely correspond to the first selected portions or may include all of the first selected portions plus additional portions. Such selective processing may be employed to elicit different desired responses in re-cellularization and in subsequent integration into a body after surgical implant or grafting.

Furthermore, any given piece of biological material, may also be uniformly processed by a single GCIB or Neutral Beam irradiation process and subsequently respond in differing positive ways to the surgical implant process according to the surgical site, application of other medicaments, or other local factors. For example a tendon used for an ACL replacement may be uniformly treated with a single GCIB or Neutral Beam irradiation process. When surgically implanted, due to local influences, some portions in contact with bone promote enhanced migration, attachment and differentiation of osteoblasts, leading to bone formation promoting integration of the tendon into the anchoring bone, while other cell types are preferentially attracted to other portions of the implanted tendon not in contact with bone. Most importantly, fibroblasts including ligamentous fibroblasts found in the synovial capsule portion (where the graft functions as a replacement ligament) are preferentially attracted to, adhere, and enter the graft, By direct application of appropriate growth and differentiation factors, such as platelet rich plasma (PRP); repulsive guidance molecules (RGMa, RGMb, and/or RGMc); cytokines including macrophage colony stimulatory factor (M-CSF), granulocyte-macrophage colony stimulatory factor (GM-CSF), interleukin-1 and -9 (IL1, IL6), or tumor necrosis factor $\alpha$ (TNF$\alpha$); members of the transforming growth factors (TGF$\beta$ super-family) including TGF$\beta$-1, TGF$\beta$-2, TGF$\beta$-3 and all the bone morphogenic proteins (BMPs), Activin A, growth differentiation factors (GDF), and Nodal; platelet derived growth factors (PDGF-AA, -AB, & -BB); fibroblast growth factors (FGFs); insulin-like growth factors (IGFs); epidermal growth factors (EGFs); or vascular endothelial growth factors (VEGFs); or by the application of demineralized bone powder containing TGFβ or members of that family, the cellular regrowth can be differentiated in favor of a desired tissue type. Alternatively, by applying concentrates in situ, for example, of mesenchymal stem cells from the fat pads found in a joint synovial space, or in the buffy coat layer of bone marrow extracted from the recipient's femur or elsewhere, regrowth of cells that naturally differentiate to the appropriate tissue for the locality is facilitated.

Figure 13:
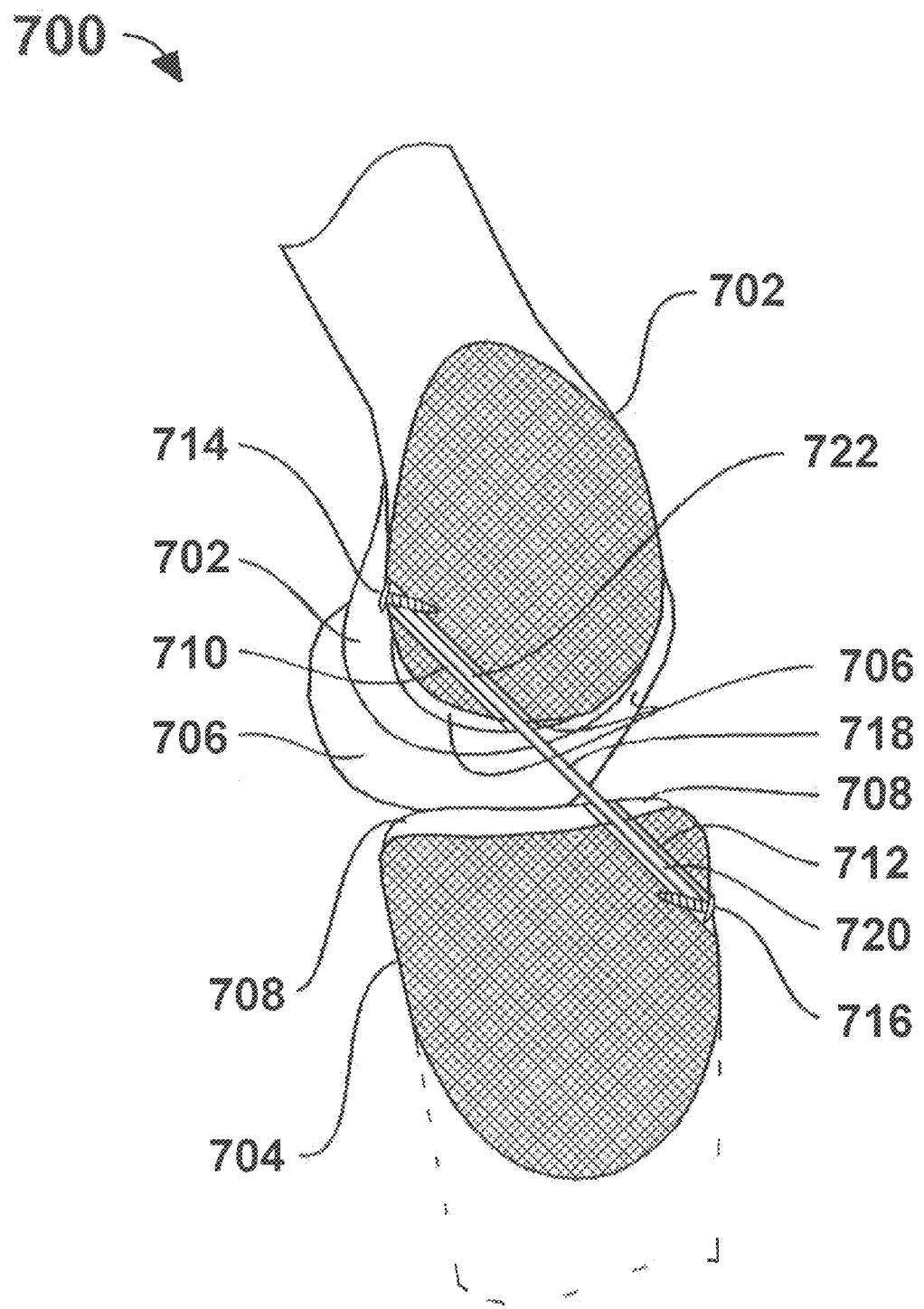
FIG. 13 is a schematic 700 of a knee joint illustrating an exemplary embodiment of beneficial application of the improved biological material of the invention.

FIG. 13 is a schematic 700 of a knee joint illustrating an exemplary embodiment of beneficial application of the improved biological materials of the invention for ligament replacement in an injured joint. The schematic is shown for illustrative purposes and is not necessarily to scale. Rupture of the anterior cruciate ligament (ACL) of a knee joint is an injury often requiring surgical grafting of a replacement for the damaged ACL. A ligament or tendon or a portion thereof may serve as the replacement graft. The graft can be derived from autologous, allogeneic, or xenogeneic tissue. There are a variety of conventional surgical repair techniques. An improved approach uses a decellularized, lyophilized, GCIB or Neutral Beam irradiated tendon or ligament tissue designated in FIG. 13 as graft 718. Schematic 700 shows a sectional view of a of an ACL replacement graft in a knee joint. The lower end of the femur 702 has femoral cartilage 706. The upper end of the tibia 704 has tibial cartilage 708. Cartilage 706 and cartilage 708 form the articulating contact surfaces of the knee joint. The crosshatched areas of femur 702 and tibia 704 represent, respectively, sectioned (for illustrative purposes only, not surgically sectioned) surfaces of the femur 702 and the tibia 704. For convenience, the section is shown taken through a plane in which the replacement graft 718 lies. Tunnels 710 and 712 are drilled in the femur 702 and the tibia 704 respectively and also penetrate the tibial cartilage 708 and femoral cartilage 706 between the bones. A variety of tunnel configurations may be employed and the configuration shown for tunnels 710 and 712 are only intended as examples. For clarity the patella is not shown and neither is the synovial capsule that encloses the joint and retains the synovial fluid that bathes all the interior surfaces of the joint. The replacement graft 718 of the invention is placed into the tunnels 710 and 712 and is fastened at the femoral end and the tibial end by fasteners 714 and 716 respectively. Any of a variety of fasteners and fixing techniques (including metal and biodegradable polymeric fasteners) may be employed and the fasteners 714 and 716 are only intended to be exemplary. The graft 718 has a femoral inserted portion 722 inserted and retained in the femoral tunnel 710 and has a tibial inserted portion 720 inserted and retained in the tibial tunnel.

In one embodiment, the decellularized, lyophilized, GCIB or Neutral Beam irradiated tissue of graft 718 is not reconstituted prior to its surgical placement and fastening in the joint. The synovial fluid (not shown) that bathes the joint is in contact with the graft 718 including both the femoral inserted portion 722 and the tibial inserted portion 720. Fibroblasts in the synovial fluid (or existing within remnant fibrils of the damaged and extirpated ACL) contact the graft 718, and attach to and proliferate within the graft 718. These fibroblasts grow and differentiate into appropriate ligamentous fibroblasts and ultimately reconstruct healthy tissue. At the femoral inserted portion 722 and the tibial inserted portion 720 of the graft 718, where the graft contacts the bone of the tunnel 712 in the tibia and the tunnel 710 in the femur the inserted portions 720 and 722 contact bone tissue containing blood and precursors of the bone osteoblasts. Osteoblasts spread on the surfaces of the inserted portions 720 and 722 of the graft 718 and attach, proliferate and differentiate into bone tissue that ultimately completely remodels and replaces graft structure in the inserted portions 720 and 722 of the graft 718.

In another embodiment, prior to surgical placement of the graft 718, the portions of the graft that will become the inserted portions 720 and 722 and/or the portions of the graft that are not to be inserted with bone may be treated with the addition of appropriate growth and differentiation factors such as platelet rich plasma (PRP); repulsive guidance molecules (RGMa, RGMb, and/or RGMc); cytokines including macrophage colony stimulatory factor (M-CSF), granulocyte-macrophage colony stimulatory factor (GM-CSF), interleukin-1 and -9 (IL1, IL6), or tumor necrosis factor α (TNFα); members of the transforming growth factors (TGFβ super-family) including TGFβ-1, TGFβ-2, TGFβ-3 and all the bone morphogenic proteins (BMPs), Activin A, growth differentiation factors (GDF), and Nodal; platelet derived growth factors (PDGF-AA, -AB, & -BB); fibroblast growth factors (FGFs); insulin-like growth factors (IGFs); epidermal growth factors (EGFs); or vascular endothelial growth factors (VEGFs). Alternatively, by applying concentrates in situ, for example, of mesenchymal stem cells from the fat pads found in a joint synovial space, or in the buffy coat layer of bone marrow extracted from the recipient's femur or elsewhere, regrowth within the graft of cells that naturally differentiate to the appropriate tissue for the locality is facilitated, for example promoting differentiation of cells that attach and proliferate in the inserted portions 720 and 722 toward the production of healthy bone.

In still another embodiment, demineralized bone powder comprising bone collagen and other non-mineral components of bone and optionally including TGF-β or members of that family, is inserted into the tunnels 710 and 712, and in contact with the inserted portions 722 and 720 of the graft 718 to promote differentiation of cells that attach and proliferate in the inserted portions 720 and 722 toward the production of healthy bone.

In a further embodiment, stem cells from the fat pads found in the joint synovial space, or in the buffy coat layer of bone marrow extracted from the patients femur or elsewhere are applied in situ to the inserted portions 720 and 722 of the graft 718 to promote differentiation of cells that attach and proliferate in the inserted portions 720 and 722 toward the production of healthy bone.

Although the invention has been described here, for exemplary purposes, in terms of certain materials including bone, ligament and tendon, it is understood that other biological materials are included within the scope of the invention. Although exemplary embodiments have been described in terms of an ACL joint repair, it is understood that a wide variety of other joint and soft tissue grafts benefit from the invention and are intended to be included in the invention. Although an embodiment of the invention has been taught in terms of fresh porcine tissues, it is readily understood by those of ordinary skill in the art that the technology employed can also be employed with routine variations to other tissues including tissues from avians and other mammals including humans, and the inventors have experimentally confirmed that the methods of the invention can be beneficially employed with frozen and/or lyophilized explant tissues as well as fresh with comparable results.

Tendon and ligament tissues are readily lyophilized using conventional techniques, well known to those of ordinary skill in the art. Lyophilized tissues offer several advantages and are therefore preferred in many potential applications of the technology of the invention. Lyophilized tissues present a smaller load on the vacuum system of the ion beam irradiation tool in preparation for and during the ion irradiation phase of the process, since such lyophilized tissues outgas less vapor than either fresh or frozen tissues. Additionally, lyophilized tissues can be stored without degradation for significant periods of time following irradiation and can be readily shipped or transported by low cost conventional shipping methods to remote sites for their surgical implantation. The lyophilized, irradiated tissues may later be reconstituted (with, for example, physiological saline or with body fluids of the recipient or other suitable fluids) at the location of the surgical procedure shortly prior to surgical implantation. Likewise, the lyophilized, irradiated tissues can be seeded with cells at the location of the surgical procedure shortly prior to surgical implantation. The reconstitution and cell seeding may even be done with cell-containing bodily fluids from the recipient's body to increase compatibility of the graft. Alternatively, the Lyophilized, irradiated tissues can be surgically grafted into the recipient in the lyophilized state, whereupon they come into contact with the recipient's bodily fluids and cells, resulting in in situ reconstitution and cell seeding of the graft tissue at the graft site. In general the long shelf life of the lyophilized, irradiated tissue offers considerable flexibility and practicality to the overall process of preparation and successful implant of graft tissues.

Graft materials explanted for use with the methods of the invention may be taken from a variety of avian and mammalian species (including human) and surgical implantation of graft materials prepared by the methods of this invention can be made into a wide variety of mammal species (including human) and, such grafts may be allografts, autografts, or xenografts, according to the respective donors and recipients of the graft tissues. The techniques for harvesting, growing and seeding new cells onto and into the tissues (including decellularized tissues and/or lyophilized tissues) may employ cells from the prospective graft recipient or from other suitable donor sources according to techniques known to those of ordinary skill in the art. The techniques of explant and decellularization employed in preparing the exemplary porcine ligaments can also be applied to tendon tissue. Accordingly, methods of the invention can be used to remove tendon, ligament or other tissues from a donor (including self-donor) or cadaver to decellularize (when desired) and lyophilize (when desired) and to seed the tissues or decellularized tissues with specific new cells for cellular attachment and proliferation according to techniques known to those of ordinary skill in the art. By use of the irradiation technology, the success of the attachment and proliferation of new cells into the graft material is significantly improved, contributing to an increased likelihood of successful integration of the graft into the recipient and increased likelihood of successful overall medical outcome.

As used herein, the term "biological material" is intended to encompass all tissue materials of biological origin including, without limitation, materials comprising tendon, ligament, bone, cartilage, soft tissues, and other tissues, decellularized or in natural cellularized state, living or dead, fresh, frozen, frozen and thawed, lyophilized, lyophilized and reconstituted, ion irradiated or not. Although the invention has been described with respect to the application of GCIBs or Neutral Beams formed with particular acceleration potentials and administered at particular doses, it will be realized by those skilled in the art that other doses and acceleration potentials may be employed and that such variations may produces variations in the degree of effects of the GCIB or Neutral Beam irradiation. Although the invention has been described with respect to the application of GCIB or Neutral Beams having gas cluster ions consisting of argon gas, it will be realized by those skilled in the art that other constituent gases and gas mixtures may also be beneficially employed. These include the noble gases, Ne, Ar, Xe, and other gases, including without limitation, the gases oxygen, nitrogen, carbon dioxide, other carbon-containing gases, both organic and inorganic and further including gas mixtures comprising any of these gases mixed with other gases and that such variation may result in variation in the degree and type of effects of the GCIB or Neutral Beam irradiation. It should be realized that this invention is also capable of a wide variety of further and other embodiments within the spirit and scope of the foregoing disclosure and the appended claims.

What is claimed is:

1. A method for preparing a biological material for implanting, said method comprising:
   providing a reduced pressure chamber;
   forming a first accelerated neutral beam within said reduced pressure chamber;
   providing a holder within said reduced pressure chamber for holding a biological material;
   positioning said biological material in said holder in said reduced pressure chamber; and
   irradiating at least a first portion of a surface of said biological material with said first accelerated neutral beam, wherein said biological material undergoes a change in properties;
   wherein the first accelerated neutral beam is separated from a first accelerated gas cluster ion beam.

2. The method of claim 1, wherein said change in properties comprises a change selected from the group consisting of:
   increased wettability of said at least a first portion of said surface;
   increased hydrophilicity of said at least a first portion of said surface;
   modified chemistry of said at least a first portion of said surface; and
   modified charge state of said at least a first portion of the surface.

3. The method of claim 1, further comprising exposing said biological material to living cells, wherein said living cells exhibit a behavior selected from the group consisting of:
   increased attachment to said at least a first portion of said surface;
      increased proliferation on said at least a first portion of said surface;
      increased penetration through or beneath said at least a first portion of said surface; and
      increased formation on or beneath said at least a first portion of said surface.

4. The method of claim 1, wherein said biological material comprises a tissue selected from the group consisting of:
   a musculoskeletal system tissue;
   a connective tissue;
   a bone tissue;
   a tendon tissue;
   a ligament tissue;
   a cartilage tissue;
   an epithelial tissue; and
   an endothelial tissue.

5. The method of claim 1, wherein said biological material comprises a cellular tissue or a decellularized tissue.

6. The method of claim 1, wherein said biological material comprises a mammalian tissue or an avian tissue.

7. The method of claim 1, wherein said first accelerated gas cluster ion beam comprises gas cluster ions comprising atoms selected from the group consisting of:
   argon;
   neon;
   xenon;
   nitrogen;
   carbon; and
   oxygen.

8. The method of claim 7, wherein:
   the first accelerated neutral beam is derived from an accelerated gas cluster ion beam having a first gas cluster ion composition and a first gas cluster ion beam acceleration potential, and the second accelerated neutral beam is derived from a gas cluster ion beam having a second gas cluster ion composition and a second gas cluster ion beam acceleration potential; and
   irradiating said at least a first portion of said surface comprises irradiating with a first accelerated neutral beam dose, and irradiating said at least a second portion of said surface comprises irradiating with a second accelerated neutral beam dose.

9. The method of claim 1, further comprising:
   forming a second accelerated neutral beam within the reduced pressure chamber; and
   irradiating at least a second portion of said surface of said biological material with said second accelerated neutral beam.

10. The method of claim 9, further comprising exposing said biological material to living cells, wherein at least a third portion of said surface is not irradiated, and wherein said living cells exposed to said at least a first portion, when compared to said living cells exposed to said at least a third portion, exhibit different behavior, said behavior comprising properties selected from the group consisting of:
   surface attachment;
   cell proliferation;
   cell surface penetration; and
   tissue formation.

\* \* \* \* \*